US011268965B2

(12) United States Patent
Kaneko et al.

(10) Patent No.: US 11,268,965 B2
(45) Date of Patent: Mar. 8, 2022

(54) MULTIPLEX BIOMARKER FOR USE IN EVALUATION OF STATE OF ACCUMULATION OF AMYLOID B IN BRAIN, AND ANALYSIS METHOD FOR SAID EVALUATION

(71) Applicants: SHIMADZU CORPORATION, Kyoto (JP); NATIONAL CENTER FOR GERIATRICS AND GERONTOLOGY, Obu (JP)

(72) Inventors: Naoki Kaneko, Kyoto (JP); Akinori Nakamura, Obu (JP)

(73) Assignees: Shimadzu Corporation, Kyoto (JP); National Center for Geriatrics and Gerontology, Aichi (JP)

( * ) Notice: Subject to any disclaimer, the term of this patent is extended or adjusted under 35 U.S.C. 154(b) by 0 days.

(21) Appl. No.: 15/752,498

(22) PCT Filed: Sep. 9, 2016

(86) PCT No.: PCT/JP2016/076706
§ 371 (c)(1),
(2) Date: Feb. 13, 2018

(87) PCT Pub. No.: WO2017/047529
PCT Pub. Date: Mar. 23, 2017

(65) Prior Publication Data
US 2018/0238909 A1    Aug. 23, 2018

(30) Foreign Application Priority Data
Sep. 16, 2015   (JP) .............................. JP2015-183372

(51) Int. Cl.
*G01N 33/68* (2006.01)
*C07K 14/47* (2006.01)
*A61P 25/28* (2006.01)

(52) U.S. Cl.
CPC ......... *G01N 33/6896* (2013.01); *G01N 33/68* (2013.01); *A61P 25/28* (2018.01); *C07K 14/47* (2013.01); *G01N 2333/4709* (2013.01); *G01N 2800/50* (2013.01); *G01N 2800/52* (2013.01); *G01N 2800/56* (2013.01); *G01N 2800/60* (2013.01)

(58) Field of Classification Search
CPC .... G01N 33/53; G01N 33/68; G01N 33/6896; G01N 2333/4709; G01N 2800/50; G01N 2800/52; G01N 2800/56; G01N 2800/60; G01N 2800/2814; G01N 2800/2821; G01N 2560/00; G01N 27/622; A61P 25/28
See application file for complete search history.

(56) References Cited

U.S. PATENT DOCUMENTS

| 2004/0014142 | A1 | 1/2004 | Vanmechelen et al. |
| 2009/0239311 | A1 | 9/2009 | Bibl et al. |
| 2011/0097319 | A1 | 4/2011 | Matsubara et al. |
| 2013/0116135 | A1 | 5/2013 | Doecke et al. |
| 2014/0378439 | A1 | 12/2014 | Dezso et al. |
| 2016/0334420 | A1 | 11/2016 | Kaneko |
| 2017/0184573 | A1 | 6/2017 | Kaneko et al. |

FOREIGN PATENT DOCUMENTS

| JP | 2002-519702 A | 7/2002 |
| JP | 2010-019864 A | 1/2010 |
| JP | 2013-063976 A1 | 4/2013 |
| JP | 2013-511732 A | 4/2013 |
| JP | 2014-095714 A | 5/2014 |
| JP | 2014-520529 A | 8/2014 |
| WO | 2011/064225 A1 | 6/2011 |
| WO | 2013/096451 A2 | 6/2013 |
| WO | WO-2015/111430 A1 | 7/2015 |
| WO | WO-2015/178398 A1 | 11/2015 |

OTHER PUBLICATIONS

Portelius E et al. Acute effect on the Abeta isoform pattern in CSF in response to gamma-secretase modulator and inhibitor treatment in dogs. J. Alzheimer's Disease, 21, 1005-1012. (Year: 2010).*
Roher AE et al. Amyloid beta peptides in human plasma and tissues and their significance for Alzheimer's disease. Alzheimer's Dementia, 5, 18-29. (Year: 2009).*
Chu LW Alzheimer's disease: early diagnosis and treatment. Hong Kong Med J. 2012, 18(3), 228-237. (Year: 2012).*

(Continued)

*Primary Examiner* — Kimberly Ballard
(74) *Attorney, Agent, or Firm* — Morgan, Lewis & Bockius LLP

(57) ABSTRACT

Provided are a biomarker for evaluating a cerebral Aβ accumulation state using amyloid precursor protein (APP)-derived Aβ and Aβ-like peptides in a living body-derived sample as an index, and a method for analysis thereof. A marker for determining a cerebral Aβ accumulation state, the marker comprising a combination of at least two ratios selected from the group consisting of: a ratio of Aβ1-39 (SEQ ID NO.: 1) level to Aβ1-42 (SEQ ID NO.: 3) level: Aβ1-39/Aβ1-42; a ratio of Aβ1-40 (SEQ ID NO.: 2) level to Aβ1-42 (SEQ ID NO.: 3) level: Aβ1-40/Aβ1-42; and a ratio of APP669-711 (SEQ ID NO.: 4) level to Aβ1-42 (SEQ ID NO.: 3) level: APP669-711/Aβ1-42, in a living body-derived sample.

14 Claims, 23 Drawing Sheets

Specification includes a Sequence Listing.

(56) References Cited

OTHER PUBLICATIONS

Galluzzi KE et al. Modern care for patients with Alzheimer disease: Rationale for early intervention. J Am Osteopath Assoc. 2010, 110(9 suppl 8), S37-S42. (Year: 2010).*

Richards SS et al. Diagnosis, management, and treatment of Alzheimer disease, A guide for the internist. Arch. Intern. Med. 1999, 156, 789-798. (Year: 1999).*

Richards SS et al. Diagnosis, management, and treatment of Alzheimer disease; A guide for the internist. Arch Intern. Med. 159, 789-798. (Year: 1999).*

Blennow et al., "Alzheimer's disease," The Lancet, vol. 368, 2006, pp. 387-403.

Graff-Radford NR, Association of low plasma AB42/AB40 ratios with increased imminent risk for mild cognitive impairment and Alzheimer disease, Arch Neurology, vol. 64, No. 3, 2007, pp. 354-362.

Hampel et al., "Biological markers of amyloid B-related mechanisms in Alzheimer's disease," Exp. Neurology, vol. 223, No. 2, 2010, pp. 334-346.

Kaneko et al., "Identification and quantification of amyloid beta-related peptides in human plasma using matrix-assisted laser desorption/ionization time-of-flight mass spectrometry," Proc. Jpn. Acad., Ser. B, vol. 90, pp. 104-117.

Kaneko et al., Novel plasma biomarker surrogating cerebral amyloid deposition, Proc. Jpn. Acad., vol. 90, No. 9, 2014, pp. 353-364.

Portelius et al., "Determination of B-Amyloid Peptide Signature in Cerebrospinal Fluid Using Immunoprecipitation-Mass Spectrometry," Journal of Proteome Research, vol. 5, 2006, pp. 1010-1016.

Van Oijen, M., Plasma AB1-40 and AB1-42 and the risk of dementia: a prospective case-cohort study, Lacet Neurology, vol. 8, No. 8, 2006, pp. 655-660.

International Search Report with English translation and Written Opinion issued in corresponding application No. PCT/JP2016/076706 dated Nov. 15, 2016.

Bibl et al., "Cerebospinal Fluid amyloid-B 2-42 is decreased in Alzheimer's, but not in frontotemporal dementia," J. Neural Transm, 2012, pp. 805-813.

Annex of Form PCT/IPEA/409 issued in corresponding application No. PCT/JP2016/076706 with English translation, 11 pages.

International Preliminary Report on Patentability issued in corresponding application No. PCT/JP2016/076706 with English translation dated Mar. 22, 2018.

Extended European Search Report issued in corresponding European patent application No. 16846400.6 dated Jan. 8, 2019.

Bibl et al., "CSF diagnosis of Alzheimer's disease and dementia with Lewy bodies," Journal of Neural Transmission; Basic Neurosciences, Genetics and Immunology, Parkinson's Disease and Allied Conditions, Alzheimer's Disease and Adolescent Psychiatry Related Disorders, Biological Psychiatry,, Biological Child and Adolescent Psychiat., vol. 113, No. 11, Aug. 17, 2006, pp. 1771-1778.

First Examination Report issued in corresponding Indian Patent Application No. 201847013746 dated Jun. 16, 2020.

Office Action issued in related Australian Patent Application No. 2019205010 dated Jun. 25, 2021.

First Examination Report issued in corresponding Indian Patent Application No. 202048054090 dated Nov. 8, 2021.

Sticht et al., "Structure of amyloid A4-(1-40)-peptide of Alzheimer's disease," European Journal of Biochemistry, 233: 293-298 (1995).

* cited by examiner

Aβ1-39/Aβ1-42 and Aβ1-40/Aβ1-42

Aβ1-39/Aβ1-42 and APP669-711/Aβ1-42

Aβ1-40/Aβ1-42 and APP669-711/Aβ1-42

Aβ1-39/Aβ1-42 and APP669-711/Aβ1-42

Aβ1-40/Aβ1-42 and APP669-711/Aβ1-42

Aβ1-39/Aβ1-42 and APP669-711/Aβ1-42

Aβ1-40/Aβ1-42 and APP669-711/Aβ1-42

Aβ1-39/Aβ1-42 and APP669-711/Aβ1-42

AUC=0.966

Aβ1-40/Aβ1-42 and APP669-711/Aβ1-42

AUC=0.912

MULTIPLEX BIOMARKER FOR USE IN EVALUATION OF STATE OF ACCUMULATION OF AMYLOID B IN BRAIN, AND ANALYSIS METHOD FOR SAID EVALUATION

CROSS REFERENCE TO RELATED APPLICATIONS

The present application is a national stage entry of International Patent Application No. PCT/JP2016/076706, filed Sep. 9, 2016, which claims priority to Japanese Patent Application No. 2015-183372, filed Sep. 16, 2015, each of which is incorporated herein by reference in its entirety.

TECHNICAL FIELD

The present invention pertains to the brain neuroscience field and the clinical medicine field, and relates to a multiplex surrogate biomarker for evaluating a cerebral amyloid β peptide (Aβ) accumulation state, and a method for analysis thereof. More specifically, the present invention relates to a multiplex surrogate biomarker for evaluating a cerebral Aβ accumulation state using, as an index, a level of Aβ and Aβ-like peptides generated by cleavage of amyloid precursor protein (APP) in a living body-derived sample, and a method for analysis thereof. The biomarker of the present invention is a marker to be used for, for example, presymptomatic diagnosis, screening for subjects of developing preventive intervention (pre-emptive therapeutic drug administration etc.) and evaluation of drug efficacy of therapeutic drugs and prophylactic drugs regarding Alzheimer's disease.

BACKGROUND ART

Alzheimer's disease (AD) is a principal cause of dementia, and occupies 50 to 60% of the entire dementia. The number of patients suffering from dementia was more than or equal to 24 million in the world in 2001, and is estimated to reach 81 million in 2040 (Non-Patent Document 1). It is considered that amyloid β (Aβ) is deeply involved in development of Alzheimer's disease. Aβ is produced as a result of proteolysis of amyloid precursor protein (APP) which is a single-pass transmembrane protein by β-secretase and γ-secretase. Appearance of senile plaques in brain due to aggregation of Aβ accompanying fibrosis triggers aggregation and accumulation of tau protein inside neurocytes to cause nerve malfunction and neuronal cell death. It is considered that this results in progressive deterioration of the cognitive ability. It has long been known that Aβ mainly consists of 40 residues (Aβ1-40) and 42 residues (Aβ1-42) and migrates into cerebrospinal fluid (CSF) and blood. Further, in recent years, existence of Aβ-like peptides having lengths different from those of Aβ1-40 and Aβ1-42 in CSF or plasma has been reported (Non-Patent Documents 2, 3).

Amyloid accumulation is considered as the earliest event among pathophysiological changes occurring in brain in the case of AD, and recent studies have revealed that amyloid accumulation in brain starts 10 years or more before onset of clinical symptoms. Therefore, it is important to exactly detect the amyloid accumulation in brain for enabling early diagnosis of AD. At present, amyloid PET and CSF Aβ examination are known as a method for detecting amyloid accumulation. The amyloid PET is a method of visualizing Aβ deposits by using a ligand molecule that specifically binds with Aβ, and an example of the amyloid PET includes PiB-PET using Pittsburgh compound-B (PiB). However, PET examination requires massive equipment, and thus an examination fee to perform one examination is high. Also, PET examination is invasive due to radiation exposure, and is not suited for a screening method of AD. On the other hand, a decrease in concentration of Aβ1-42 in CSF or a decrease in concentration ratio of Aβ1-42/Aβ1-40, and an increase in total tau value or phosphorylation tau value are reported to be a useful marker (Patent Document 1: JP-A-2010-19864, Non-Patent Document 4). However, collection of CSF is also highly invasive, and is not suited as a screening method of AD. Therefore, a blood examination that has low invasiveness and is low in cost is desired for the screening.

Under these circumstances, the potentiality of concentration of Aβ1-42 existing in blood as an Alzheimer's disease diagnostic marker is expected, and many researchers have reported the relationship between blood Aβ1-42 concentration and Alzheimer's disease development; however, consistent results have not been obtained (Non-Patent Document 4).

However, in recent years, a ratio of APP669-711/Aβ1-42 was reported as a promising blood marker that reflects a cerebral amyloid accumulation state (Non-Patent Document 5). Non-Patent Document 5 indicates that the ratio of APP669-711/Aβ1-42 has a strong correlation with a PiB accumulation degree obtained by PiB-PET. Further, the results of ROC analysis between a PiB positive group and a PiB negative group indicate that the ratio of APP669-711/Aβ1-42 is a marker capable of accurately distinguishing between a PiB positive person and a PiB negative person.

Also, Patent Document 2: JP-A-2013-63976 discloses a monoclonal antibody that does not recognize a soluble Aβ monomer, but specifically binds only to a soluble Aβ oligomer, and also discloses a diagnostic method of Alzheimer's disease using the antibody. Paragraph [0104] of the publication discloses a method in which when the ratio of Aβ oligomer to Aβ monomer in a sample of a subject is higher than that of a normal healthy person, the subject is determined as being a candidate for Alzheimer's disease.

Patent Document 3: JP-T-2014-520529 discloses a method for diagnosing Alzheimer's disease by combining a plurality of miRNA levels in a sample obtained from an object.

PRIOR ART DOCUMENTS

Patent Documents

Patent Document 1: JP-A-2010-19864
Patent Document 2: JP-A-2013-63976
Patent Document 3: JP-T-2014-520529

Non-Patent Documents

Non-Patent Document 1: Blennow K, de Leon M J, Zetterberg H.: Alzheimer's disease. Lancet. 2006 Jul. 29; 368 (9533): 387-403
Non-Patent Document 2: Portelius E, Westman-Brinkmalm A, Zetterberg H, Blennow K.: Determination of beta-amyloid peptide signatures in cerebrospinal fluid using immunoprecipitation-mass spectrometry. J Proteome Res. 2006 April; 5(4): 1010-6
Non-Patent Document 3: Kaneko N, Yamamoto R, Sato T A, Tanaka K.: Identification and quantification of amyloid beta-related peptides in human plasma using matrix-assisted laser desorption/ionization time-of-flight mass spectrometry. Proc Jpn Acad Ser B Phys Biol Sci. 2014; 90(3):104-17.

Non-Patent Document 4: Hampel H, Shen Y, Walsh D M, Aisen P, Shaw L M, Zetterberg H, Trojanowski J Q, Blennow K.: Biological markers of amyloid beta-related mechanisms in Alzheimer's disease. Exp Neurol. 2010 June; 223(2): 334-46

Non-Patent Document 5: Kaneko N, Nakamura A, Washimi Y, Kato T, Sakurai T, Arahata Y, Bundo M, Takeda A, Niida S, Ito K, Toba K, Tanaka K, Yanagisawa K.: Novel plasma biomarker surrogating cerebral amyloid deposition. Proc Jpn Acad Ser B Phys Biol Sci. 2014; 90(9): 353-64.

SUMMARY OF THE INVENTION

Problems to be Solved by the Invention

It has been found that a large quantity of Aβ has been deposited before exteriorization of the cognitive function decline in an Alzheimer's disease (AD) patient. Although Amyloid-PET is effective for detecting Aβ accumulation, it requires high examination cost and long time for executing the examination, and thus is not a diagnostic method that allows for a majority of elderly people to easily undergo the examination. Therefore, a simplified analytical method capable of detecting increase in Aβ accumulation before exteriorization of clinical symptoms has been demanded.

As described above, generally, an examination method using a biomarker existing in blood or cerebrospinal fluid (CSF) as an index is an effective method capable of conveniently detecting the development and progression of a disease on the molecular level. Patent Document 1 and Non-Patent Document 4 described above have reported that in Alzheimer's disease, a decrease in concentration of Aβ1-42 in CSF is a useful diagnostic marker. On the other hand, however, Non-Patent Document 4 has also reported that the relationship between blood Aβ1-42 concentration and AD development is low unlike the case of CSF Aβ1-42.

Conventionally, in previous reports regarding Aβ in blood, the correlativity with AD has been examined only for concentrations of two kinds of Aβ1-40 and Aβ1-42 in blood. In Non-Patent Document 5 described above, the ratio of APP669-711/Aβ1-42 was reported as a promising blood marker that reflects a cerebral amyloid accumulation state. While cerebral amyloid accumulation can be determined with high sensitivity by the ratio of APP669-711/Aβ1-42, a method that enables more accurate discrimination is demanded.

An object of the present invention is to provide a biomarker for evaluating a cerebral Aβ accumulation state using amyloid precursor protein (APP)-derived Aβ and Aβ-like peptides in a living body-derived sample as an index, and a method for analysis thereof. In particular, an object of the present invention is to provide a biomarker for evaluating a cerebral Aβ accumulation state using amyloid precursor protein (APP)-derived Aβ and Aβ-like peptides in a blood sample as an index, and a method for analysis thereof. More specifically, an object of the present invention is to provide a marker to be used for, for example, presymptomatic diagnosis, screening for subjects of developing preventive intervention (pre-emptive therapeutic drug administration etc.) and evaluation of drug efficacy of therapeutic drugs and prophylactic drugs regarding Alzheimer's disease, and a method for analysis thereof.

Means for Solving the Problems

As a result of diligent studies, the present inventors have completed the present invention by calculating a numerical value by a combination of two or more ratios selected from the group consisting of three ratios, Aβ1-39/Aβ1-42, Aβ1-40/Aβ1-42, and APP669-711/Aβ1-42, regarding Aβ and Aβ-like peptides derived from APP in a living body sample, through a mathematical technique.

In the present description, "Aβ" is used as an abbreviation of an amyloid β peptide. That is, "Aβ" includes Aβ1-40 and Aβ1-42. A peptide other than the Aβ generated by cleavage of amyloid precursor protein (APP) may be referred to as an Aβ-like peptide. Aβ and an Aβ-like peptides that are generated by cleavage of amyloid precursor protein (APP) may be referred to as "APP-derived peptide".

The present invention includes the following aspects.

(1) A marker for determining a cerebral Aβ accumulation state, the marker comprising a combination of at least two ratios selected from the group consisting of:
a ratio of Aβ1-39 (SEQ ID NO.: 1) level to Aβ1-42 (SEQ ID NO.: 3) level: Aβ1-39/Aβ1-42;
a ratio of Aβ1-40 (SEQ ID NO.: 2) level to Aβ1-42 (SEQ ID NO.: 3) level: Aβ1-40/Aβ1-42; and
a ratio of APP669-711 (SEQ ID NO.: 4) level to Aβ1-42 (SEQ ID NO.: 3) level: APP669-711/Aβ1-42, in a living body-derived sample.

More specifically, a marker for determining a cerebral Aβ accumulation state, the marker comprising a mathematically obtained composite variable of at least two ratios selected from the group consisting of:
a ratio of Aβ1-39 (SEQ ID NO.: 1) level to Aβ1-42 (SEQ ID NO.: 3) level: Aβ1-39/Aβ1-42;
a ratio of Aβ1-40 (SEQ ID NO.: 2) level to Aβ1-42 (SEQ ID NO.: 3) level: Aβ1-40/Aβ1-42; and
a ratio of APP669-711 (SEQ ID NO.: 4) level to Aβ1-42 (SEQ ID NO.: 3) level: APP669-711/Aβ1-42, in a living body-derived sample.

The marker according to the above (1), wherein the living body-derived sample is selected from the group consisting of blood, cerebrospinal fluid, urine, feces, and body secreting fluid (e.g., saliva, tear, sweat, nasal mucosal exudate, and sputum).

(2) An analytical method for determining a cerebral Aβ accumulation state, the method comprising:
a measurement step of subjecting a living body-derived sample derived from a test subject to detection of a marker containing:
  Aβ1-42 (SEQ ID NO.: 3); and
  at least two selected from the group consisting of Aβ1-39 (SEQ ID NO.: 1), Aβ1-40 (SEQ ID NO.: 2), and APP669-711 (SEQ ID NO.: 4),
to obtain measurement levels of:
  Aβ1-42; and
  the at least two selected from the group consisting of Aβ1-39, Aβ1-40, and APP669-711, in the living body-derived sample;
a calculation step of calculating at least two ratios selected from the group consisting of:
  a ratio of Aβ1-39 level to Aβ1-42 level: Aβ1-39/Aβ1-42;
  a ratio of Aβ1-40 level to Aβ1-42 level: Aβ1-40/Aβ1-42; and
  a ratio of APP669-711 level to Aβ1-42 level: APP669-711/Aβ1-42;

a derivation step of deriving a composite variable by a combination of each of the ratios calculated, through a mathematical technique; and an evaluation step of determining that an amount of cerebral Aβ accumulation of the test subject is larger than an amount of cerebral Aβ accumulation of a person who is negative for cerebral Aβ accumulation, when the composite variable of the test subject is higher than a standard level which is the composite variable of the person who is negative for cerebral Aβ accumulation.

(3) An analytical method for determining efficacy of a medical intervention regarding a cerebral Aβ accumulation state, the method comprising:

conducting examination, each of before and after a medical intervention performed for a test subject, the examination including:
- a measurement step of subjecting a living body-derived sample derived from the test subject to detection of a marker containing:
  - Aβ1-42 (SEQ ID NO.: 3); and
  - at least two selected from the group consisting of Aβ1-39 (SEQ ID NO.: 1), Aβ1-40 (SEQ ID NO.: 2), and APP669-711 (SEQ ID NO.: 4),
- to obtain measurement levels of:
  - Aβ1-42; and
  - the at least two selected from the group consisting of Aβ1-39, Aβ1-40, and APP669-711, in the living body-derived sample;
- a calculation step of calculating at least two ratios selected from the group consisting of:
  - a ratio of Aβ1-39 level to Aβ1-42 level: Aβ1-39/Aβ1-42;
  - a ratio of Aβ1-40 level to Aβ1-42 level: Aβ1-40/Aβ1-42; and
  - a ratio of APP669-711 level to Aβ1-42 level: APP669-711/Aβ1-42; and
- a derivation step of deriving a composite variable by a combination of each of the ratios calculated, through a mathematical technique; and comparing the composite variable of the test subject before the medical intervention and the composite variable of the test subject after the medical intervention to determine efficacy of the medical intervention regarding a cerebral Aβ accumulation state.

That is, it can be determined that the medical intervention is efficacious regarding a cerebral Aβ accumulation state when the composite variable of the test subject after the medical intervention is smaller than the composite variable of the test subject before the medical intervention.

(4) An analytical method for predicting progression of symptoms in future or predicting a risk of development of dementia regarding a cerebral Aβ accumulation state, the method comprising:

conducting examination once or a plurality of times over time for a test subject, the examination including:
- a measurement step of subjecting a living body-derived sample derived from the test subject to detection of a marker containing:
  - Aβ1-42 (SEQ ID NO.: 3); and
  - at least two selected from the group consisting of Aβ1-39 (SEQ ID NO.: 1), Aβ1-40 (SEQ ID NO.: 2), and APP669-711 (SEQ ID NO.: 4),
- to obtain measurement levels of:
  - Aβ1-42; and
  - the at least two selected from the group consisting of Aβ1-39, Aβ1-40, and APP669-711, in the living body-derived sample;
- a calculation step of calculating at least two ratios selected from the group consisting of:
  - a ratio of Aβ1-39 level to Aβ1-42 level: Aβ1-39/Aβ1-42;
  - a ratio of Aβ1-40 level to Aβ1-42 level: Aβ1-40/Aβ1-42; and
  - a ratio of APP669-711 level to Aβ1-42 level: APP669-711/Aβ1-42; and
- a derivation step of deriving a composite variable by a combination of each of the ratios calculated, through a mathematical technique; and predicting progression of symptoms in future or predicting a risk of development of dementia regarding a cerebral Aβ accumulation state of the test subject based on a value(s) of the composite variable of the test subject in once or a plurality of times conducted over time.

That is, even in the case where the examination including the aforementioned respective steps is conducted only once, it is possible to predict progression of symptoms of Alzheimer's disease in the future or to predict a risk of development of dementia from the value of the composite variable. Further, in the case where the examination including the aforementioned respective steps is conducted a plurality of times over time, it is possible to predict progression of symptoms of Alzheimer's disease in the future or to predict a risk of development of dementia with higher accuracy from the values of the composite variable.

(5) The analytical method according to any one of the above (2) to (4), wherein the mathematical technique is a method using discriminant analysis (linear discriminant analysis, quadratic discriminant analysis, normalized discriminant analysis), multiple regression analysis, principal components regression analysis (PCA), PLS (partial least squares regression), or logistic regression.

(6) The analytical method according to any one of the above (2) to (4), wherein the mathematical technique is a method of normalizing each of the aforementioned ratios, and then deriving a mean value or a total value of the at least two ratios normalized.

(7) The analytical method according to any one of the above (2) to (6), wherein the living body-derived sample is selected from the group consisting of blood, cerebrospinal fluid, urine, feces, and body secreting fluid (e.g., saliva, tear, sweat, nasal mucosal exudate, and sputum).

In the present invention, the term "level of marker" basically means a concentration, but may be other units applied correspondingly to concentration by a person skilled in the art. The term "test subject" includes human, and mammals other than human (rat, dog, cat etc.). In the present invention, the living body-derived sample is disposed of rather than being returned to the test subject (for example, subject) from which the biological sample is derived. The medical intervention includes administration of a therapeutic drug or a prophylactic drug, dietetic therapy, exercise therapy, learning therapy, surgical operation and the like.

Effects of the Invention

The present invention provides a marker for determining a cerebral Aβ accumulation state, including a combination of at least two ratios selected from the group consisting of:
a ratio of Aβ1-39 level to Aβ1-42 level: Aβ1-39/Aβ1-42;
a ratio of Aβ1-40 level to Aβ1-42 level: Aβ1-40/Aβ1-42; and
a ratio of APP669-711 level to Aβ1-42 level: APP669-711/Aβ1-42, in a living body-derived sample. The present invention also provides a method for analysis of the marker.

By combining at least two ratios selected from the group consisting of three ratios in a living body-derived sample of a test subject: Aβ1-39/Aβ1-42, Aβ1-40/Aβ1-42, and APP669-711/Aβ1-42, it is possible to estimate a cerebral Aβ accumulation state with higher accuracy, as compared with the case where each of the three ratios is used singly. The composite variable using a mathematical technique can be obtained by combining at least two ratios selected from the group consisting of Aβ1-39/Aβ1-42, Aβ1-40/Aβ1-42, and APP669-711/Aβ1-42 with a weighting estimated from a statistical view, or with an equivalent weighting, and a cerebral Aβ accumulation state can be estimated more accurately from each of the ratios.

The present invention is applicable to detection of not only the advanced stage of Alzheimer's disease in which cerebral Aβ is excessively accumulated and a cognitive functional disorder has appeared, but also a mild cognitive impairment (MCI) which is an early stage of the advanced stage of Alzheimer's disease, and further a preclinical stage of Alzheimer's disease in which cerebral Aβ is excessively accumulated but a cognitive functional disorder has not been appeared.

According to the present invention, as the living body-derived sample, not only blood, but also cerebrospinal fluid (CSF), urine, faces, and body secreting fluid (e.g., saliva, tear, sweat, nasal mucosal exudate, and sputum) can be used. Therefore, in the stage where the preventive method and the pre-emptive therapeutic method for Alzheimer's disease have established, analysis of a cerebral Aβ accumulation state for a person having normal cognitive function in a general medical examination, a complete physical examination and the like is effective for presymptomatic diagnosis of Alzheimer's disease.

By applying the present invention before and after a medical intervention performed for the test subject, it is possible to evaluate the drug efficacy of a therapeutic drug or a prophylactic drug for Alzheimer's disease, or to evaluate the efficacy of other treatment. Also, the present invention is useful for follow-up of a patient suffering from Alzheimer's disease.

By applying the present invention to the test subject once or a plurality of times over time, it is possible to predict progression of symptoms of Alzheimer's disease in the future or to predict a risk of development of dementia.

MODES FOR CARRYING OUT THE INVENTION

[1. Test Subject]

Figure 1:
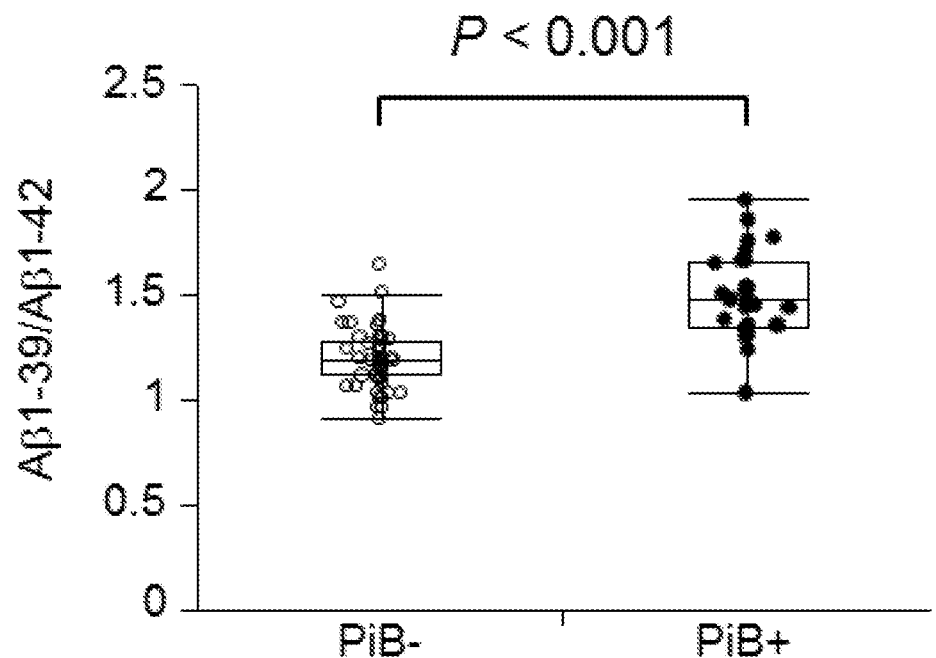
FIG. 1 is a box-and-whisker plot showing comparison between the group PiB− and the group PiB+ for Aβ1-39/Aβ1-42 in Experimental Example 1.

In the present invention, the test subject includes human, and mammals other than human (rat, dog, cat etc.). Hereinafter, the description will be made mainly for the case of human, but the same applies to mammals other than human.

In the method of the present invention, the subject may be any individuals including a person expected to be a normal healthy person regardless of past clinical history. For a person expected to be a normal healthy person, a cerebral Aβ accumulation state can be determined in a general medical examination, or a complete physical examination, preferably by a blood test, and the method is particularly effective for early detection/diagnosis of Alzheimer's disease. For a subject suspected to be a candidate for Alzheimer's disease as a result of ADAS-cog, MMSE, DemTect, SKT, or a test of cognitive function such as a clock drawing test for examining clinical symptom, and confirmation of image findings of magnetic resonance imaging diagnosis (MRI), positron emission tomography (PET) and the like, the method of the present invention can be used as a determination material for diagnosing Alzheimer's disease more accurately from the viewpoint of a fundamental view such as the presence or absence of a cerebral amyloid lesion.

[2. Living Body-Derived Sample]

The marker of the present invention can be detected and analyzed in a living body-derived sample of a subject. Therefore, in the method of the present invention, a level of a marker in a living body-derived sample of a subject is analyzed.

The living body-derived sample can be selected from blood, cerebrospinal fluid (CSF), urine, faces, body secreting fluid (e.g., saliva, tear, sweat, nasal mucosal exudate, and sputum) and the like. Among these, blood is preferred for diagnosis and presymptomatic diagnosis of Alzheimer's disease in a general medical examination, a complete physical examination or the like.

The blood sample is a sample that is directly subjected to a measurement step of expression level of a marker, and includes whole blood, plasma, serum and the like. The blood sample can be prepared by appropriately treating whole blood collected from a test subject. The treatment performed in the case of preparing a blood sample from collected whole blood is not particularly limited, and any treatment that is clinically acceptable, such as centrifugal separation may be performed. The blood sample subjected to the measurement step may be appropriately stored at a low temperature such as freezing in the intermediate stage of the preparation step or in the post stage of the preparation step. In the present invention, the living body-derived sample such as a blood sample is disposed of rather than being returned to the subject from which it is derived.

[3. Marker]

The marker of the present invention comprises a composite variable using a mathematical technique from at least two ratios selected from the group consisting of:

a ratio of Aβ1-39 level to Aβ1-42 level: Aβ1-39/Aβ1-42;

a ratio of Aβ1-40 level to Aβ1-42 level: Aβ1-40/Aβ1-42; and a ratio of APP669-711 level to Aβ1-42 level: APP669-711/Aβ1-42, in a living body-derived sample. For the marker including a composite variable using a mathematical technique from these at least two ratios, a significant difference has been observed between the composite variable level in the plasma sample from a person having normal cognitive function who is negative for cerebral Aβ accumulation and the composite variable level in the plasma sample from a subject having excessively accumulated cerebral Aβ.

APP672-710 (Aβ1-39) (SEQ ID NO.: 1): DAEFRHDSGYEVHHQKLVFFAEDVGSNKGAIIGLMVGGV

APP672-711 (Aβ1-40) (SEQ ID NO.: 2): DAEFRHDSGYEVHHQKLVFFAEDVGSNKGAIIGLMVGGVV

APP672-713 (Aβ1-42) (SEQ ID NO.: 3): DAEFRHDSGYEVHHQKLVFFAEDVGSNKGAIIGLMVGGVVIA

APP669-711 (SEQ ID NO.: 4): VKMDAEFRHDSGYEVHHQKLVFFAEDVGSNKGAIIGLMVGGVV

Amyloid precursor protein (APP) is a single-pass transmembrane protein and is composed of 770 amino acid residues. Amyloid precursor protein (APP) is proteolyzed by β secretase and γ secretase, and an amyloid β peptide (Aβ) is produced by the proteolysis. APP672-713 and Aβ1-42 indicate the same peptide (SEQ ID NO.: 3). APP672-711 and Aβ1-40 indicate the same peptide (SEQ ID NO.: 2).

[4. Analysis of Marker]

A method for analysis of the marker of the present invention includes:

a measurement step of subjecting a living body-derived sample derived from a test subject to detection of a marker containing:

Aβ1-42 (SEQ ID NO.: 3); and at least two selected from the group consisting of Aβ1-39 (SEQ ID NO.: 1), Aβ1-40 (SEQ ID NO.: 2), and APP669-711 (SEQ ID NO.: 4), to obtain measurement levels of:

Aβ1-42; and the at least two selected from the group consisting of Aβ1-39, Aβ1-40, and APP669-711 in the living body-derived sample;

a calculation step of calculating at least two ratios selected from the group consisting of:

a ratio of Aβ1-39 level to Aβ1-42 level: Aβ1-39/Aβ1-42;

a ratio of Aβ1-40 level to Aβ1-42 level: Aβ1-40/Aβ1-42; and a ratio of APP669-711 level to Aβ1-42 level: APP669-711/Aβ1-42;

a derivation step of deriving a composite variable by a combination of each of the ratios calculated, through a mathematical technique; and an evaluation step of determining that an amount of cerebral Aβ accumulation of the test subject is larger than an amount of cerebral Aβ accumulation of a person who is negative for cerebral Aβ accumulation, when the composite variable of the test subject is higher than a standard level which is the composite variable of the person who is negative for cerebral Aβ accumulation. This makes it possible to determine a cerebral Aβ accumulation state, or to use the marker as a determination material.

The term "level of marker" basically means a concentration, but may be other units applied correspondingly to concentration by a person skilled in the art, for example, a detected ion intensity in the mass spectrometry. In the present invention, the marker in the living body-derived sample is analyzed by comparing the composite variable derived from a measurement value (measurement composite variable) and the composite variable derived from a standard value (standard composite variable). For more accurate analysis, it is preferred that the measurement value and the standard value to be compared are values based on the living body-derived samples prepared in the same conditions (pretreatment condition, storage condition and the like). As the standard composite variable of the marker, a composite variable that is derived from a measurement value for a person determined as negative for cerebral Aβ accumulation by a PiB-PET image can be used. Alternatively, as the standard composite variable of the marker, a standard composite variable established for a normal person who is negative for cerebral Aβ accumulation by a PiB-PET image can be used.

A marker is measured, preferably, by a test based on biological molecule specific affinity. The test based on biological molecule specific affinity is a method well known to a person skilled in the art and is not particularly limited, but is preferably an immunoassay. Specific examples of the immunoassay include competitive and non-competitive assays such as western blotting, radioimmunoassay, ELISA (Enzyme-Linked ImmunoSorbent Assay) (sandwich immunoassay, competitive assay, and direct binding assay are included), immunoprecipitation, precipitation reaction, immunodiffusion, immunoagglutination measurement, complement-binding reaction analysis, immunoradiometric assay, fluorescence immunoassay, and protein A immunoassay. In the immunoassay, an antibody that binds to the marker in a living body-derived sample is detected.

In the present invention, the measurement of the marker may be performed by using an immunoglobulin having an antigen binding site capable of recognizing an amyloid precursor protein (APP)-derived peptide, or an antibody-immobilizing carrier prepared by using an immunoglobulin fragment having an antigen binding site capable of recognizing an amyloid precursor protein (APP)-derived peptide. By immunoprecipitation using the antibody-immobilizing carrier, a peptide in the sample can be detected by a mass spectrometer (Immunoprecipitation-Mass Spectrometry: IP-MS).

In the present invention, consecutive immunoprecipitation (cIP) may be conducted, and then a peptide in the sample may be detected by a mass spectrometer (cIP-MS). By conducting affinity purification twice consecutively, impurities that cannot be excluded by one affinity purification can be further reduced by the second affinity purification. Therefore, it is possible to prevent the ionization suppression of polypeptide due to impurities, and it becomes possible to measure even a very small amount of polypeptide in a living body sample with high sensitivity by mass spectrometry.

By combining at least two ratios selected from the group consisting of three ratios in a living body-derived sample of a test subject: Aβ1-39/Aβ1-42, Aβ1-40/Aβ1-42, and APP669-711/Aβ1-42, it is possible to estimate a cerebral 4 accumulation state with higher accuracy, as compared with the case where each of the three ratios is used singly. The composite variable using a mathematical technique can be obtained by combining at least two ratios selected from the group consisting of Aβ1-39/Aβ1-42, Aβ1-40/Aβ1-42, and APP669-711/Aβ1-42 with a weighting estimated from a statistical view, or with an equivalent weighting, and a cerebral Aβ accumulation state can be estimated more accurately from each of the ratios.

As the mathematical technique for combination with a weighting estimated from a statistical view, for example, using at least two ratios selected from the three ratios, a composite variable is calculated by discriminant analysis, multiple regression analysis, principal components regression analysis, partial least square, or logistic regression. This can be a combined composite variable.

As the mathematical technique for combination with an equal weighting, for example, for at least two ratios selected from the three ratios, the ratios are normalized, and then a mean value or a total value of the at least two ratios normalized is derived, and the derived mean value or total value is given as a composite variable of the at least two ratios. More specifically, for at least two ratios selected from the three ratios, normalization based on all cases of the test subject is conducted, or normalization based on the control group (PiB-group: a group determined as being negative for cerebral Aβ accumulation by a PiB-PET image) is conducted, and then a mean value of the at least two ratios normalized (z-score) is calculated, and this may be a combined composite variable.

By using such a mathematical technique, even when one ratio of at least two ratios selected from the three ratios is too large or too small as compared with the other one or two ratios, it is possible to combine these ratios with an equal weighting, and by using the composite variable combined, it is possible to estimate the cerebral Aβ accumulation state more accurately from each of the aforementioned ratios.

EXAMPLES

Hereinafter, the present invention will be described specifically with reference to examples, but is not limited to these examples. In the following, the amount of a matter indicated by % is based on weight when the matter is solid, and based on volume when the matter is liquid unless otherwise indicated.

Experimental Example 1

[1-1. Plasma Sample]

Plasma samples (76 specimens) of cases classified into groups of PiB− and PiB+ were prepared at National Center for Geriatrics and Gerontology.

PiB− (person determined as negative for cerebral Aβ accumulation by PiB-PET image): 50 cases PiB+ (person determined as positive for cerebral Aβ accumulation by PiB-PET image): 26 cases In order to determine the positivity or negativity of cerebral Aβ accumulation, PiB-PET images of the brains of the subjects were acquired. When the PiB accumulation amount of the cerebral cortex is larger than or equivalent to the non-specific PiB accumulation amount of the white matter, the subject was determined as positive. When only non-specific accumulation to the white matter was observed, and little accumulation was observed in the cortex, the subject was determined as negative. The cognitive impairment was determined in conformity with the NIA-AA criteria published in 2011.

Regarding PiB accumulation mean value (mcSUVR: mean cortical Standard Uptake Value Ratio), cortical PiB accumulation was quantified, and an accumulation ratio of cerebrum based on cerebellum was determined. However, in PiB−, there were two cases of missing values.

[1-2. Preparation of Antibody-Immobilizing Beads]

Clone 6E10 (available from Covance) of an anti-Aβ antibody (IgG) recognizing 3-8 residues of amyloid β protein (Aβ) as an epitope was prepared.

For 100 μg of an anti-Aβ antibody (IgG), about $3.3 \times 10^8$ magnetic beads (Dynabeads (registered trademark) M-270 Epoxy) were reacted in an immobilizing buffer (0.1 M phosphate buffer containing 1 M ammonium sulfate (pH 7.4)) at 37° C. for 16 to 24 hours, to prepare anti-Aβ IgG immobilizing beads.

[1-3. Consecutive Immunoprecipitation (cIP)]

(First Reaction Step)

Into 250 μL of human plasma, 250 μL of a first IP reaction buffer (0.2% (w/v) DDM, 0.2% (w/v) NTM, 800 mM GlcNAc, 100 mM Tris-HCl, 300 mM NaCl, pH 7.4) containing 10 pM stable isotope labeled Aβ1-38 (SIL-Aβ1-38) was mixed, and then the mixture was allowed to stand for 5 to 30 minutes on ice. SIL-Aβ1-38 in which carbon atoms in Phe and Ile are substituted by $^{13}C$ was used as an internal standard for standardization of signal intensity of a mass spectrum. The plasma was mixed with anti-Aβ IgG immobilizing beads, and shaken for 1 hour on ice.

(First Washing Step, First Elution Step)

Then, the antibody beads were washed three times with 100 μL of a first IP washing buffer (0.1% DDM, 0.1% NTM, 50 mM Tris-HCl (pH 7.4), 150 mM NaCl), and washed twice with 50 μL of a 50 mM ammonium acetate buffer, and then Aβ and Aβ-like peptides (namely, APP-derived peptides) bound to the antibody beads were eluted with a first IP eluent (50 mM Glycine buffer containing 0.1% DDM (pH 2.8)).

(Neutralization Step)

The obtained eluate was mixed with a second IP reaction buffer (0.2% (w/v) DDM, 800 mM GlcNAc, 300 mM Tris-HCl, 300 mM NaCl, pH 7.4), to obtain a first purified solution.

(Second Reaction Step)

The obtained first purified solution was mixed with another anti-Aβ antibody immobilizing beads, and shaken for 1 hour on ice.

(Second Washing Step, Second Elution Step)

Then, the anti-Aβ antibody immobilizing beads were washed five times with 50 μL of a second washing buffer (0.1% DDM, 50 mM Tris-HCl (pH 7.4), 150 mM NaCl), washed twice with 50 μL of a 50 mM ammonium acetate buffer, and washed once with 30 μL of $H_2O$, and then Aβ and Aβ-like peptides (APP-derived peptides) bound to the antibody beads were eluted with 5 μL of a second IP eluent (70% (v/v) acetonitrile containing 5 mM hydrochloric acid). In this manner, a second purified solution was obtained. The second purified solution was subjected to mass spectrometry.

n-Dodecyl-β-D-maltoside (DDM) [critical micelle concentration (cmc): 0.009%]

n-Nonyl-β-D-thiomaltoside (NTM) [cmc: 0.116%]

[1-4. Detection by MALDI-TOF MS]

As a matrix for Linear TOF, α-cyano-4-hydroxycinnamic acid (CHCA) was used. A matrix solution was prepared by dissolving 1 mg of CHCA in 1 mL of 70% (v/v) acetonitrile. As a matrix additive, 0.4% (w/v) methanediphosphonic acid (MDPNA) was used. After mixing equivalent amounts of a 1 mg/mL CHCA solution and 0.4% (w/v) MDPNA, 0.5 μL of the resultant mixture was dropped on a μFocus MALDI Plate™ 900 μm (Hudson Surface Technology, Inc., Fort Lee, N.J.) and dried and solidified.

One µL of the second purified solution obtained by the aforementioned immunoprecipitation was dropped into the matrix on the µFocus MALDI Plate™ 900 µm.

Mass spectrum data was acquired by Linear TOF in a positive ion mode by using AXIMA Performance (Shimadzu/KRATOS, Manchester, UK). For 1 well, 400 spots, or 16,000 shots were integrated. A criterion of a detection limit of a peak was an S/N ratio of 3 or more. An m/z value of Linear TOF was indicted by an average mass of a peak. An m/z value was calibrated by using human angiotensin II and human ACTH fragment 18-39, bovine insulin oxidized beta-chain, and bovine insulin as external standards.

[1-5. Normalization of Peak Intensities of Aβ and Aβ-Like Peptides]

In each mass spectrum, by dividing a signal intensity of each of Aβ and Aβ-like peptides (APP-derived peptide) by a signal intensity of the internal standard peptide (SIL-Aβ1-38), signal intensities of Aβ and Aβ-like peptides were normalized. Thereafter, a mean value of normalized intensity of each APP-derived peptide obtained from four mass spectra per one specimen was calculated, and used in a statistical analysis. Among the four normalized intensities used in averaging, a normalized intensity that is out of the range of 0.7 to 1.3 times of the median was regarded as an outlier, and removed in the data processing for averaging. When the number of data of normalized intensity to be used in averaging is less than 3 because the data does not reach the detection lower limit (S/N<3), or an outlier occurs, the analysis result is "undetectable".

[1-6. Statistics]

For comparison between group the PiB− and the group PiB+, evaluation using a t-test was conducted. For evaluating the performance of discriminating between PiB− and PiB+, an area under the curve (AUC), a sensitivity (Sensitivity), a specificity (Specificity), and an accuracy (Accuracy) were determined using a Receiver Operatorating Characteristic (ROC) curve. Every test was conducted by a two-sided test, and $P<0.05$ was used as a significant level. Correlation analysis between each marker value and mcSUVR was evaluated with Pearson product-moment correlation coefficient. However, there were two cases of missing values in mcSUVR, so that analysis was conducted for 74 cases.

[1-7. Comparison Between Groups for Each Marker]

Figure 2:
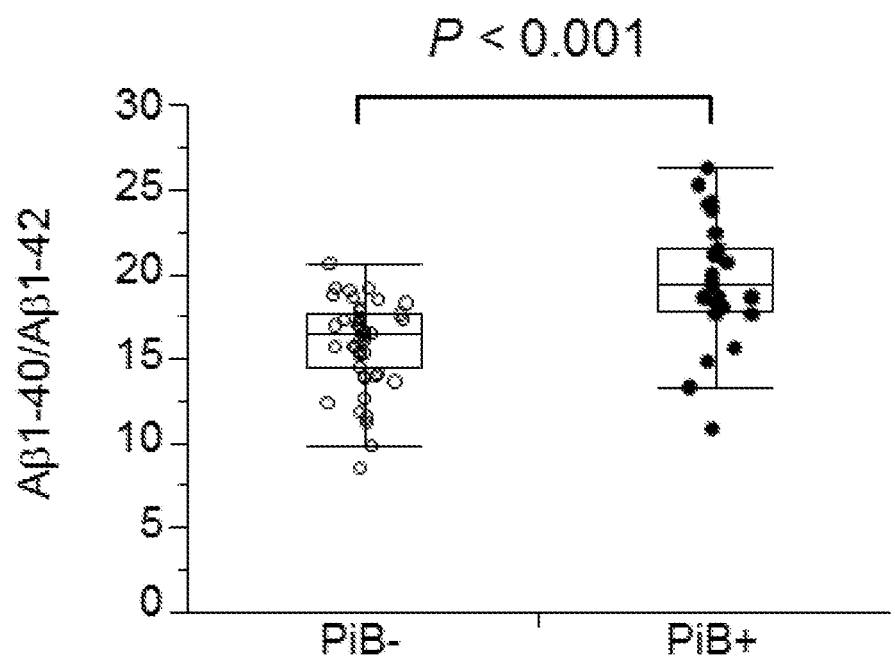
FIG. 2 is a box-and-whisker plot showing comparison between the group PiB− and the group PiB+ for Aβ1-40/Aβ1-42 in Experimental Example 1.
Figure 3:
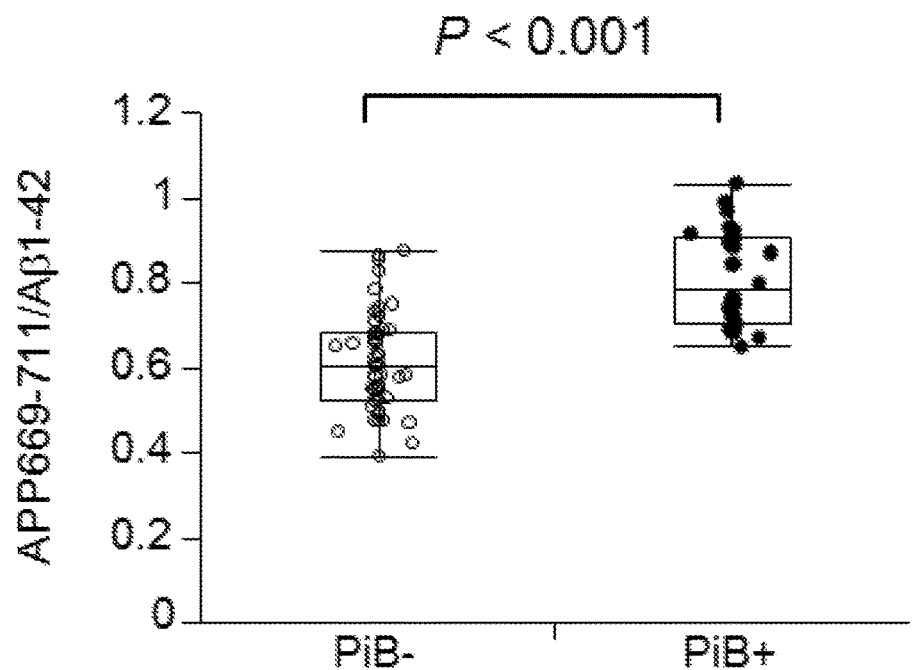
FIG. 3 is a box-and-whisker plot showing comparison between the group PiB− and the group PiB+ for APP669-711/Aβ1-42 in Experimental Example 1.

Using a ratio of a normalized intensity of Aβ1-39, Aβ1-40, or APP669-711 to a normalized intensity of Aβ1-42 (i.e., Aβ1-39/Aβ1-42, Aβ1-40/Aβ1-42, APP669-711/Aβ1-42) as a marker, comparison between the group PiB− and the group PiB+ was conducted (FIGS. 1, 2, 3). Any P value obtained in the t-test satisfied $P<0.001$, revealing that the value increased statistically significantly in PiB+ as compared with PiB−.

FIG. 1 is a box-and-whisker plot showing comparison between the group PiB− and the group PiB+ for Aβ1-39/Aβ1-42. Likewise, FIG. 2 is a box-and-whisker plot showing comparison between the group PiB− and the group PiB+ for Aβ1-40/Aβ1-42. FIG. 3 is a box-and-whisker plot showing comparison between the group PiB− and the group PiB+ for APP669-711/Aβ1-42. These are results for a single marker.

In each box-and-whisker plot, the range indicated by the box in each group represents the intensity ratio contribution range (quartile range) of the samples whose intensity ratio is rated between 25 to 75% of all specimens, and the horizontal lines shown above and below the box respectively indicate the maximum value and the minimum value of the samples within the range from the upper end and the lower end of the box to 1.5 times the quartile range, and the horizontal bar in the box indicates the median of the intensity ratio. The same applies in each box-and-whisker plot below.

[1-8. ROC Analysis for Each Marker]

Figure 4:
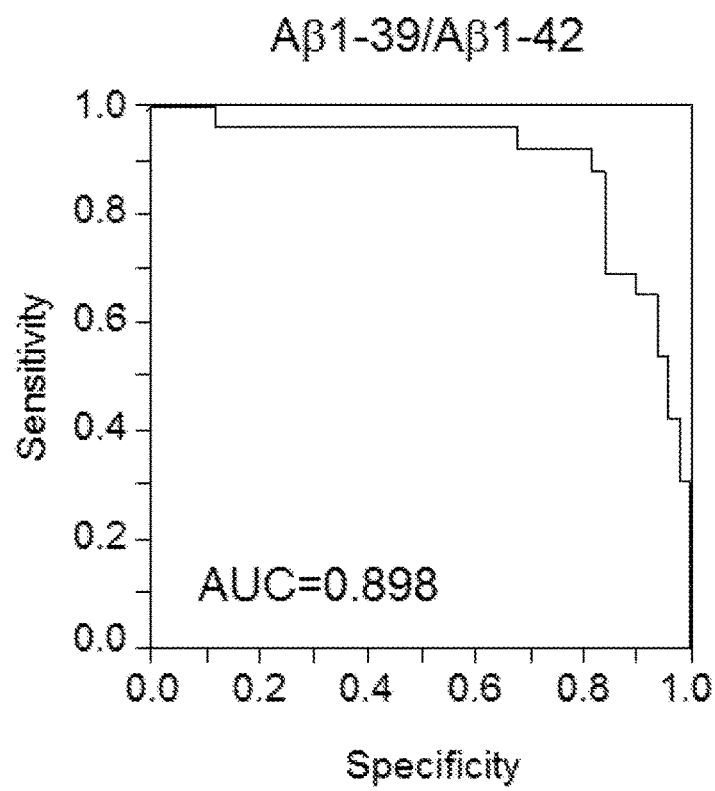
FIG. 4 is an ROC curve for Aβ1-39/Aβ1-42 in Experimental Example 1.
Figure 5:
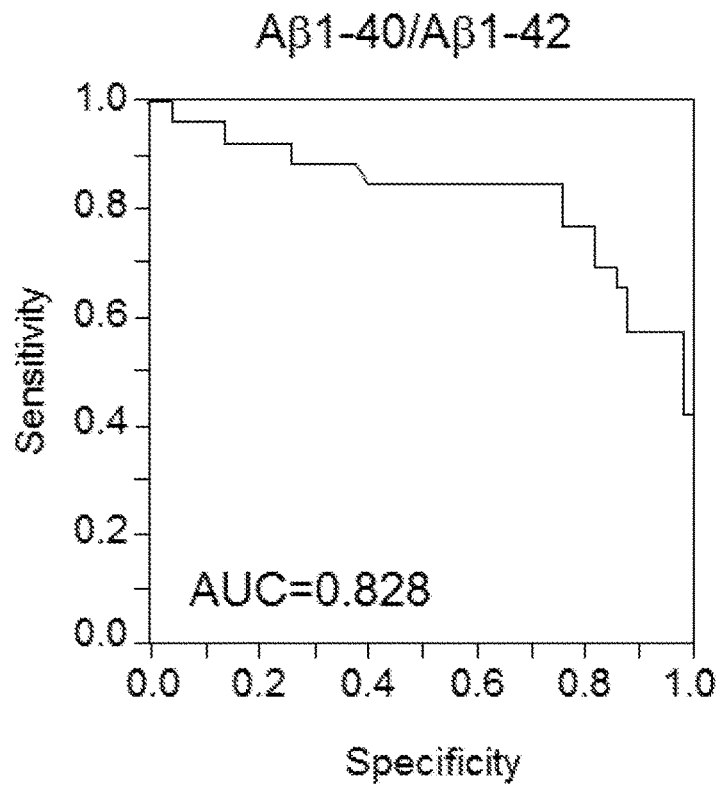
FIG. 5 is an ROC curve for Aβ1-40/Aβ1-42 in Experimental Example 1.
Figure 6:
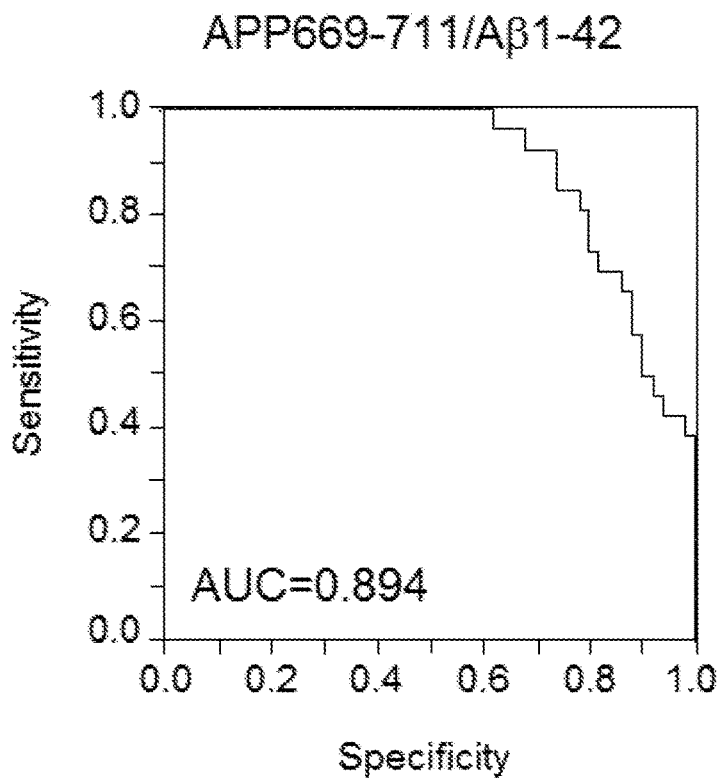
FIG. 6 is an ROC curve for APP669-711/Aβ1-42 in Experimental Example 1.

For evaluating the determination performance of Aβ1-39/Aβ1-42, Aβ1-40/Aβ1-42, and APP669-711/Aβ1-42, ROC analysis of the group PiB+ versus the group PiB− was conducted with PiB+ as positive (FIGS. 4, 5, 6). As a result, Aβ1-39/Aβ1-42 showed the highest AUC=0.898, APP669-711/Aβ1-42 showed the second highest AUC=0.894, and Aβ1-40/Aβ1-42 showed AUC=0.828. The AUC was 0.8 or more for any marker, and this reveals that the markers are capable of discrimination between the group PiB− and the group PiB+ with high accuracy.

FIG. 4 is an ROC curve for Aβ1-39/Aβ1-42. Likewise, FIG. 5 is an ROC curve for Aβ1-40/Aβ1-42. FIG. 6 is an ROC curve for APP669-711/Aβ1-42. These are results for a single marker.

In an ROC curve of each marker, the value showing the highest "sensitivity+specificity−1" was set as a cut-off value. The set cut-off values, and Sensitivity, Specificity, and Accuracy at each cut-off value are shown in Table 1. Aβ1-39/Aβ1-42 showed the highest Accuracy=0.855. In Table 1, Numbers 1 to 3 show analysis of a single marker.

TABLE 1

| No. | Single Marker | | | AUC | Correlation coefficient (r) | Cut-off | Sensitivity | Specificity | Accuracy |
| | Aβ1-39/ Aβ1-42 | Aβ1-40/ Aβ1-42 | APP669-711/ Aβ1-42 | | | | | | |
| --- | --- | --- | --- | --- | --- | --- | --- | --- | --- |
| 1 | X | | | 0.898 | 0.630 | 1.311 | 0.923 | 0.820 | 0.855 |
| 2 | | X | | 0.828 | 0.477 | 17.587 | 0.808 | 0.760 | 0.789 |
| 3 | | | X | 0.894 | 0.489 | 0.684 | 0.923 | 0.740 | 0.803 |

[1-9. Correlation Analysis Between Each Marker Value and mcSUVR]

Figure 7:
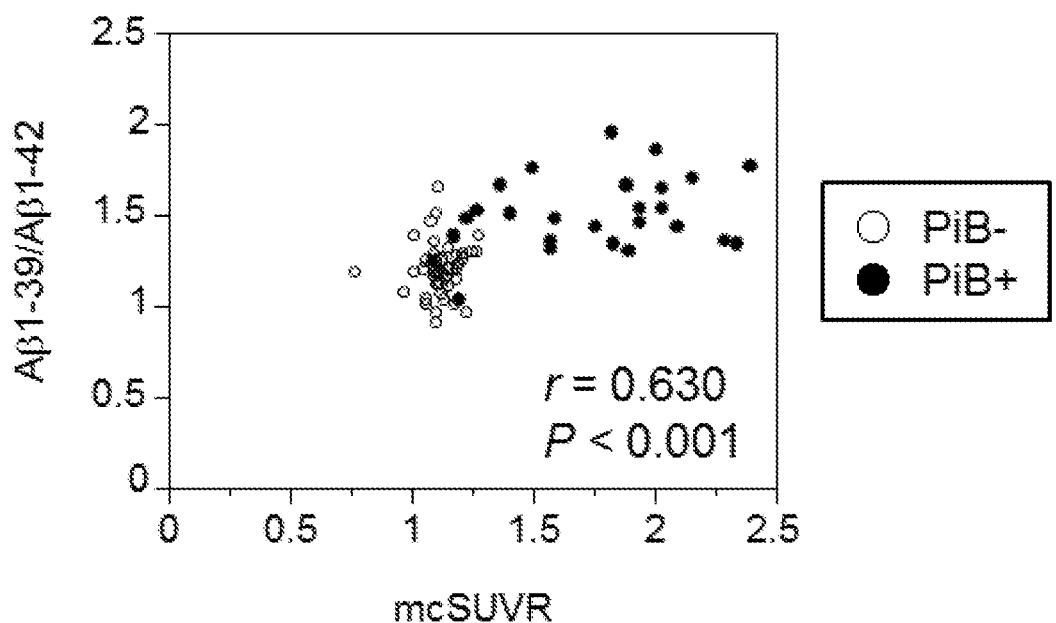
FIG. 7 is a scatter diagram of PiB accumulation mean value (mcSUVR) and Aβ1-39/Aβ1-42 ratio in Experimental Example 1.
Figure 8:
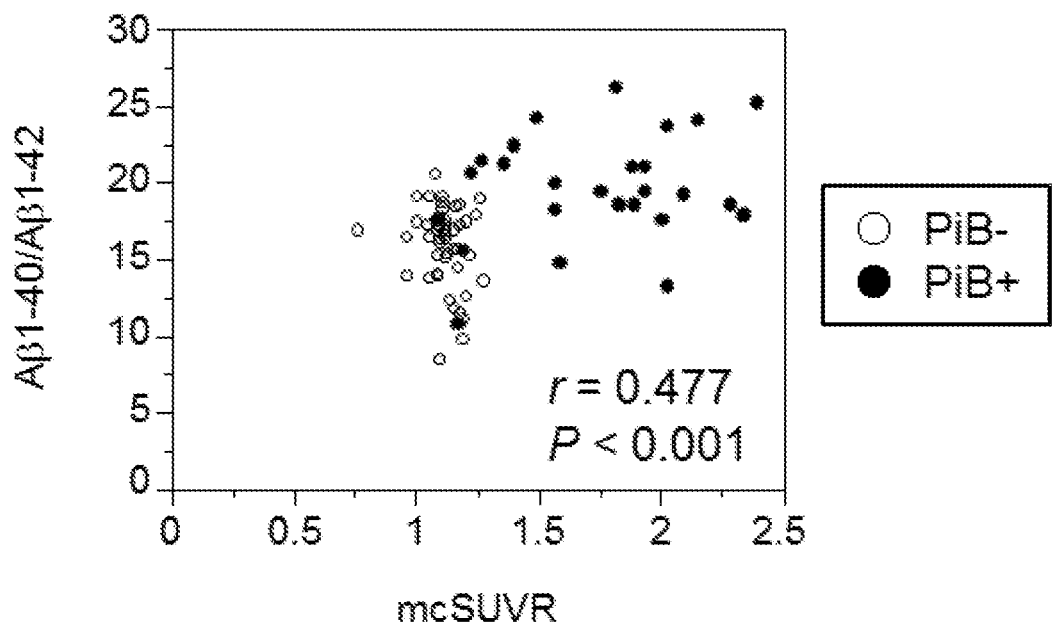
FIG. 8 is a scatter diagram of PiB accumulation mean value (mcSUVR) and Aβ1-40/Aβ1-42 ratio in Experimental Example 1.
Figure 9:
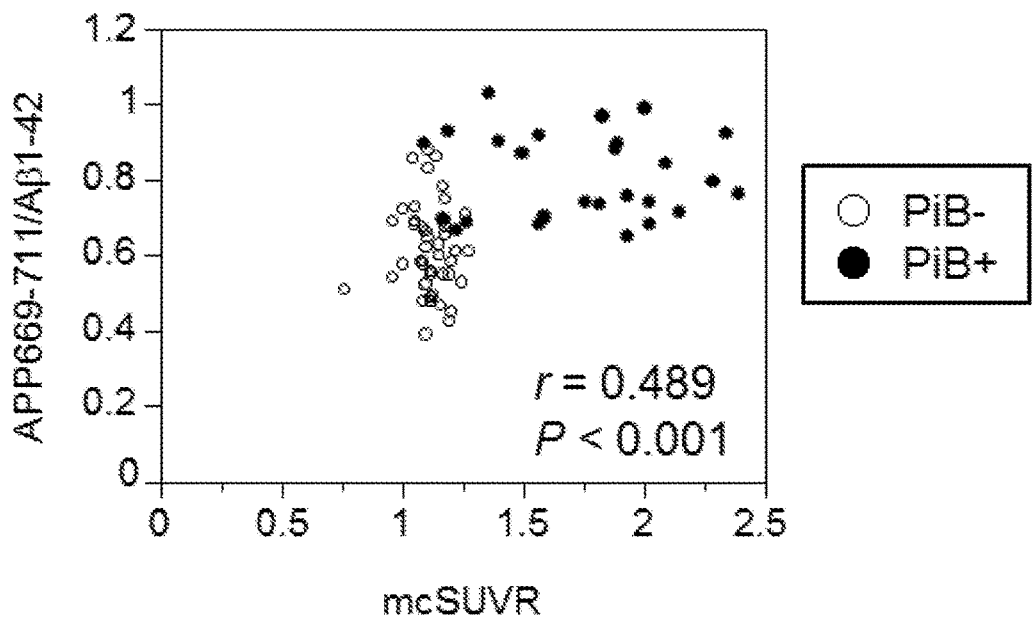
FIG. 9 is a scatter diagram of PiB accumulation mean value (mcSUVR) and APP669-711/Aβ1-42 ratio in Experimental Example 1.

In order to investigate whether Aβ1-39/Aβ1-42, Aβ1-40/Aβ1-42, and APP669-711/Aβ1-42 reflect a cerebral amyloid accumulation amount, correlation between each index and mcSUVR was analyzed (FIGS. 7, 8, 9, Table 1). As a result, in all the three markers, the Pearson product-moment correlation coefficient (r) was 0.4 or more, and existence of correlation was proved, and in particular, the correlation coefficient (r) of Aβ1-39/Aβ1-42 showed the strongest correlation of 0.630.

This indicates that Aβ1-39/Aβ1-42, Aβ1-40/Aβ1-42, and APP669-711/Aβ1-42 have the potential to be an index that is useful for determination of a cerebral amyloid accumulation state. In the present analysis for the 76 cases, Aβ1-39/Aβ1-42 showed the most excellent determination performance.

FIG. 7 is a scatter diagram for Aβ1-39/Aβ1-42, in which the horizontal axis represents PiB accumulation mean value (mcSUVR) and the vertical axis represents Aβ1-39/Aβ1-42 ratio. Likewise, FIG. 8 is a scatter diagram for Aβ1-40/Aβ1-42, in which the horizontal axis represents PiB accumulation mean value (mcSUVR) and the vertical axis represents Aβ1-40/Aβ1-42 ratio. FIG. 9 is a scatter diagram for APP669-711/Aβ1-42, in which the horizontal axis represents PiB accumulation mean value (mcSUVR) and the vertical axis represents APP669-711/Aβ1-42 ratio. These are results for a single marker. In the diagram, "○" indicates the group PiB−, and "●" indicates the group PiB+. The same applies to the following scatter diagrams.

[1-10. Method for Combining Markers Using Discriminant Analysis]

Discriminant analysis was conducted by using combinations of two markers, Aβ1-39/Aβ1-42 and Aβ1-40/Aβ1-42, Aβ1-39/Aβ1-42 and APP669-711/Aβ1-42, and Aβ1-40/Aβ1-42 and APP669-711/Aβ1-42, and a combination of three markers Aβ1-39/Aβ1-42, Aβ1-40/Aβ1-42 and APP669-711/Aβ1-42, and discriminant function z in each combination was obtained. A discriminant score was calculated from marker values to be combined by using discriminant function z.

A discriminant score was calculated from marker values to be combined by using discriminant function z, and then subsequent statistical analysis was conducted.

[1-11. Comparison Between Groups by Discriminant Score]

For discriminant scores obtained by combinations of markers, comparison between the groups PiB− and PiB+ was conducted (FIGS. 10, 11, 12, 13). Any P value obtained in the t-test satisfied P<0.001, and it was confirmed that even in the case of combination, the value increased statistically significantly in the group PiB+ compared with the group PiB−.

Figure 10:
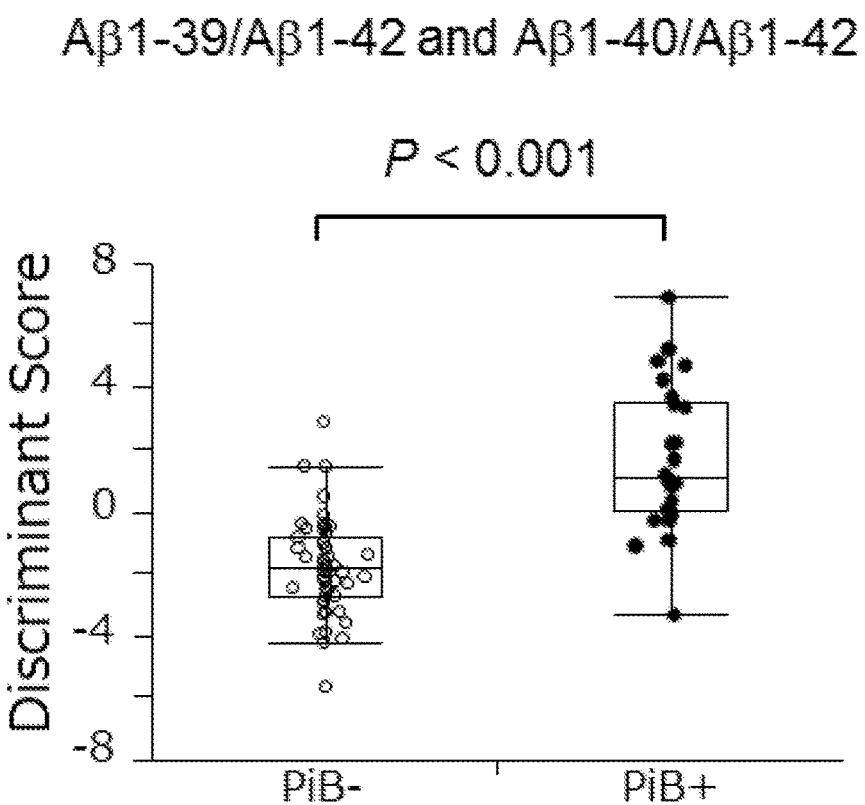
FIG. 10 is a box-and-whisker plot showing comparison between the group PiB− and the group PiB+ for a combination of two markers: Aβ1-39/Aβ1-42 and Aβ1-40/Aβ1-42 in Experimental Example 1.
Figure 11:
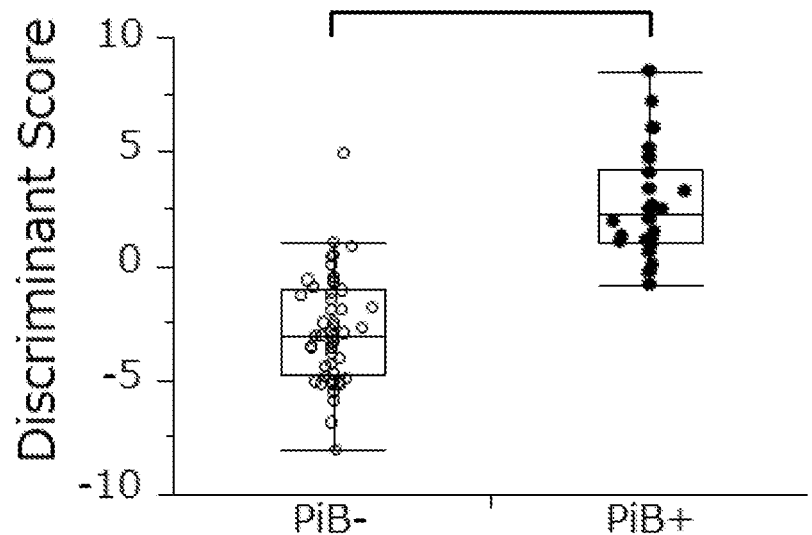
FIG. 11 is a box-and-whisker plot showing comparison between the group PiB− and the group PiB+ for a combination of two markers: Aβ1-39/Aβ1-42 and APP669-711/Aβ1-42 in Experimental Example 1.
Figure 12:
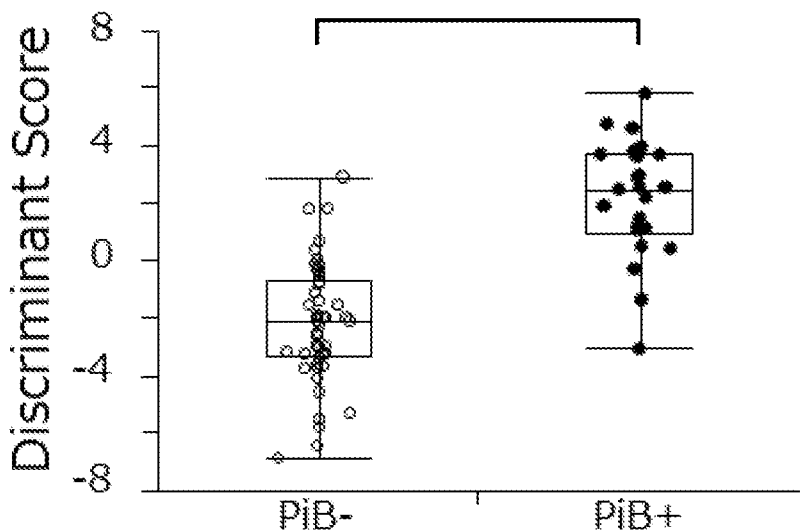
FIG. 12 is a box-and-whisker plot showing comparison between the group PiB− and the group PiB+ for a combination of two markers: Aβ1-40/Aβ1-42 and APP669-711/Aβ1-42 in Experimental Example 1.
Figure 13:
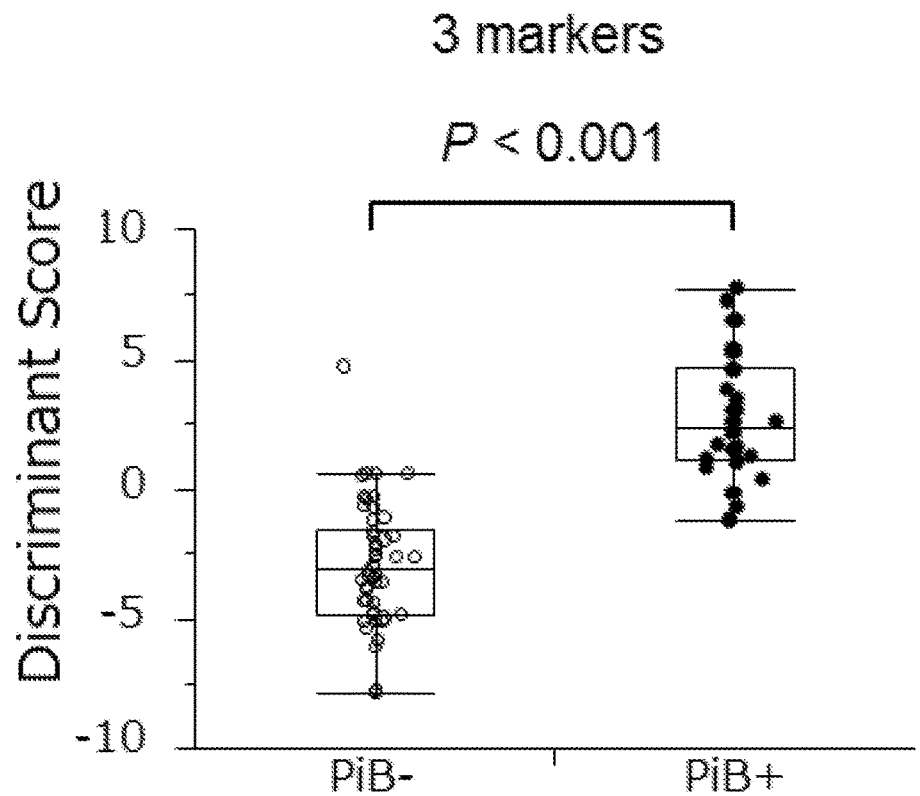
FIG. 13 is a box-and-whisker plot showing comparison between the group PiB− and the group PiB+ for a combination of three markers: Aβ1-39/Aβ1-42, Aβ1-40/Aβ1-42, and APP669-711/Aβ1-42 in Experimental Example 1.

FIG. 10 is a box-and-whisker plot showing comparison between the group PiB− and the group PiB+ for a combination of two markers: Aβ1-39/Aβ1-42 and Aβ1-40/Aβ1-42. Likewise, FIG. 11 is a box-and-whisker plot showing comparison between the group PiB− and the group PiB+ for a combination of two markers: Aβ1-39/Aβ1-42 and APP669-711/Aβ1-42. FIG. 12 is a box-and-whisker plot showing comparison between the group PiB− and the group PiB+ for a combination of two markers: Aβ1-40/Aβ1-42 and APP669-711/Aβ1-42. FIG. 13 is a box-and-whisker plot showing comparison between the group PiB− and the group PiB+ for a combination of three markers: Aβ1-39/Aβ1-42, Aβ1-40/Aβ1-42 and APP669-711/Aβ1-42.

[1-12. ROC Analysis by Discriminant Score]

For evaluating the determination performance of discriminant scores, ROC analysis of the group PiB+ versus the group PiB− was conducted with PiB+ as positive (FIGS. 14, 15, 16, 17). As a result, combinations of two makers, Aβ1-39/Aβ1-42 and Aβ1-40/Aβ1-42 (FIG. 14), Aβ1-39/Aβ1-42 and APP669-711/Aβ1-42 (FIG. 15), Aβ1-40/Aβ1-42 and APP669-711/Aβ1-42 (FIG. 16), and a combination of three markers (FIG. 17) each showed an AUC of 0.9 or more, which is higher than that by a single marker (FIGS. 14, 15, 16, 17, Table 2). That is, by combining markers, the discrimination performance improved and discrimination between PiB− and PiB+ with very high accuracy was enabled. In the present ROC analysis, the combination of Aβ1-39/Aβ1-42 and APP669-711/Aβ1-42 showed the highest AUC.

Figure 14:
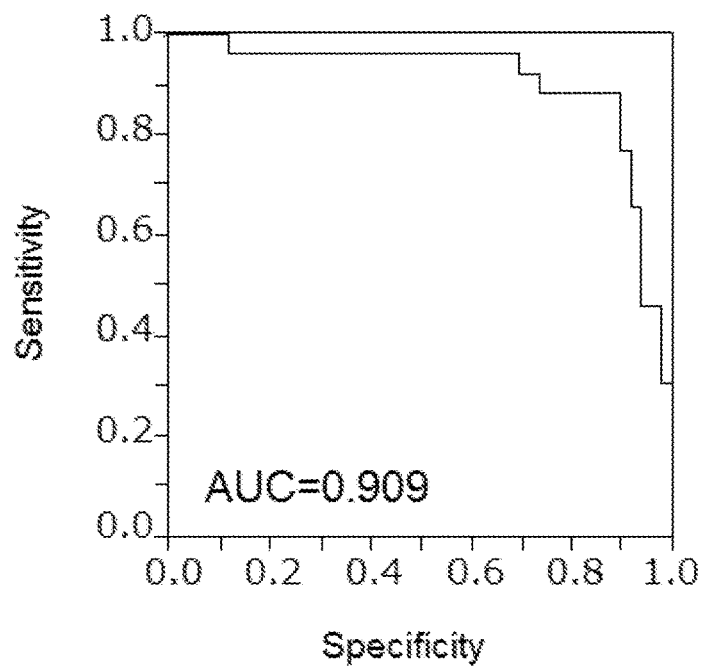
FIG. 14 is an ROC curve for a combination of two markers: Aβ1-39/Aβ1-42 and Aβ1-40/Aβ1-42 in Experimental Example 1.
Figure 15:
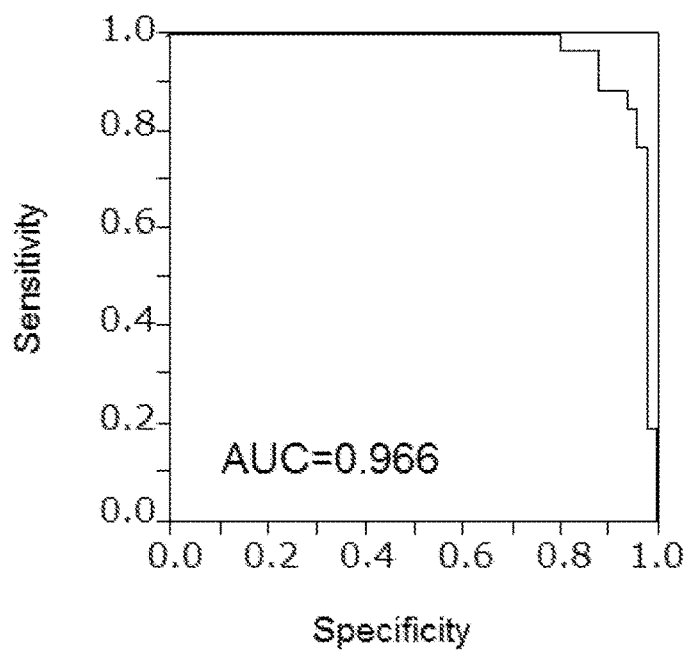
FIG. 15 is an ROC curve for a combination of two markers: Aβ1-39/Aβ1-42 and APP669-711/Aβ1-42 in Experimental Example 1.
Figure 16:
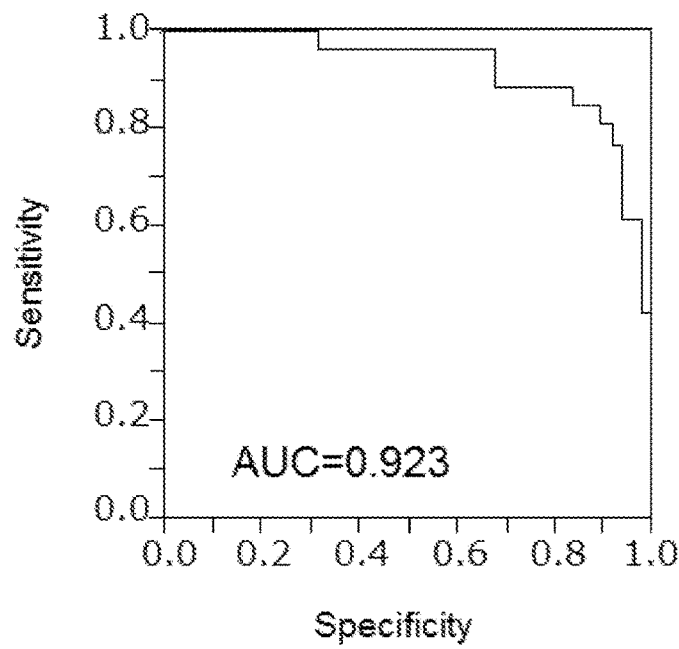
FIG. 16 is an ROC curve for a combination of two markers: Aβ1-40/Aβ1-42 and APP669-711/Aβ1-42 in Experimental Example 1.
Figure 17:
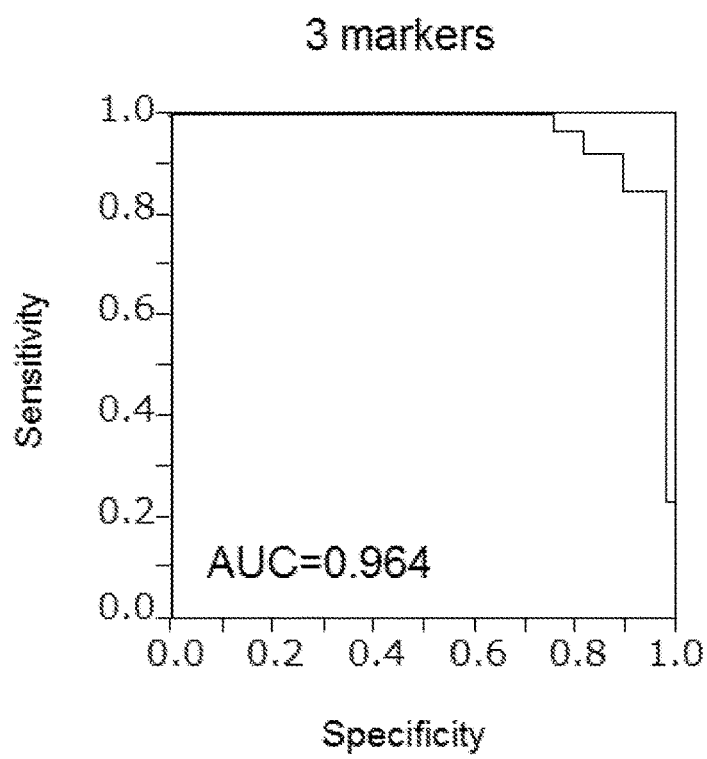
FIG. 17 is an ROC curve for a combination of three markers: Aβ1-39/Aβ1-42, Aβ1-40/Aβ1-42, and APP669-711/Aβ1-42 in Experimental Example 1.

FIG. 14 is an ROC curve for a combination of two markers: Aβ1-39/Aβ1-42 and Aβ1-40/Aβ1-42. Likewise, FIG. 15 is an ROC curve for a combination of two markers: Aβ1-39/Aβ1-42 and APP669-711/Aβ1-42. FIG. 16 is an ROC curve for a combination of two markers: Aβ1-40/Aβ1-42 and APP669-711/Aβ1-42. FIG. 17 is an ROC curve for a combination of three markers: Aβ1-39/Aβ1-42, Aβ1-40/Aβ1-42 and APP669-711/Aβ1-42.

The discriminant score>0 is discriminated as PiB+, and the discriminant score<0 is discriminated as PiB−. That is, Sensitivity, Specificity, and Accuracy in each combination when the cut-off value is set at 0 are shown in Table 2 (Numbers: 11, 12, 13, 14). All the combinations showed Accuracy that is higher than that by a single marker. That is, by combining markers, the probability of exact determination was improved. In the present analysis, the combination of three markers showed the highest Accuracy. In Table 2, Numbers 11 to 14 show the results obtained by conducting discriminant analysis by using each marker value, and using a discriminant score of combined markers for analysis.

TABLE 2

| No. | Combination of Markers | | | AUC | Correlation coefficient (r) | Cut-off | Sensitivity | Specificity | Accuracy |
| | Aβ1-39/ Aβ1-42 | Aβ1-40/ Aβ1-42 | APP669-711/ Aβ1-42 | | | | | | |
|---|---|---|---|---|---|---|---|---|---|
| 11 | X | X | | 0.909 | 0.634 | 0 | 0.769 | 0.920 | 0.868 |
| 12 | X | | X | 0.966 | 0.653 | 0 | 0.923 | 0.880 | 0.895 |
| 13 | | X | X | 0.923 | 0.581 | 0 | 0.846 | 0.880 | 0.868 |
| 14 | X | X | X | 0.964 | 0.656 | 0 | 0.885 | 0.900 | 0.895 |

[1-13. Correlation Analysis with mcSUVR by Discriminant Score]

In order to investigate whether discriminant scores of combined markers reflect a cerebral amyloid accumulation amount, correlation between each discriminant score and mcSUVR was analyzed. Combinations of two markers, Aβ1-39/Aβ1-42 and Aβ1-40/Aβ1-42, Aβ1-39/Aβ1-42 and APP669-711/Aβ1-42, and Aβ1-40/Aβ1-42 and APP669-711/Aβ1-42, as well as a combination of three markers each showed improved Pearson product-moment correlation coefficient (r) as compared with that by a single marker, and reflected the PiB accumulation degree more favorably (FIGS. 18, 19, 20, 21, Table 2). In the present correlation analysis, the combination of three markers showed the highest correlation coefficient.

Figure 18:
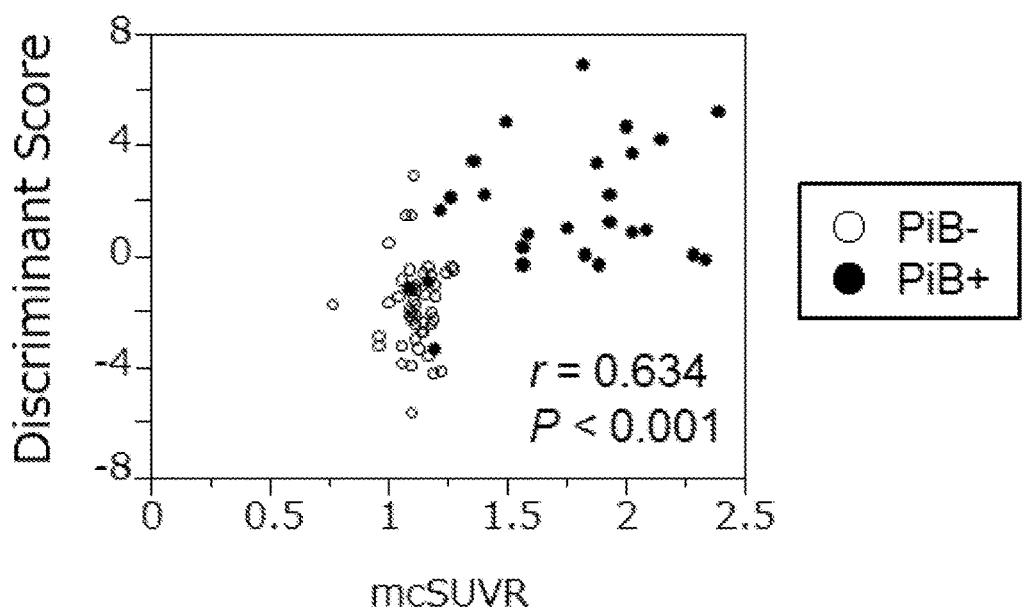
FIG. 18 is a scatter diagram of PiB accumulation mean value (mcSUVR) and discriminant score of a combination of Aβ1-39/Aβ1-42 and Aβ1-40/Aβ1-42 in Experimental Example 1.
Figure 19:
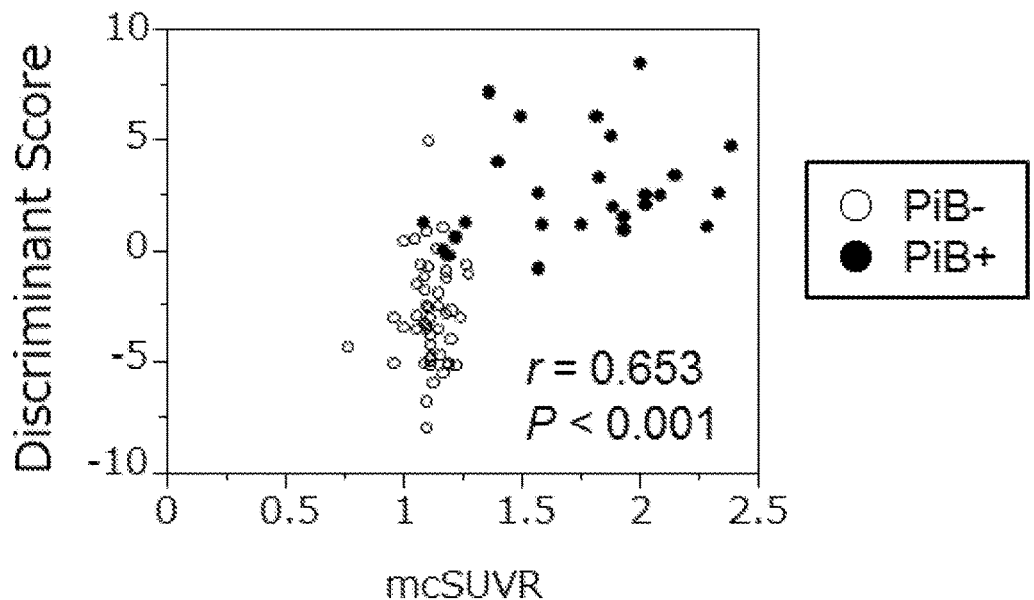
FIG. 19 is a scatter diagram of PiB accumulation mean value (mcSUVR) and discriminant score of a combination of Aβ1-39/Aβ1-42 and APP669-711/Aβ1-42 in Experimental Example 1.
Figure 20:
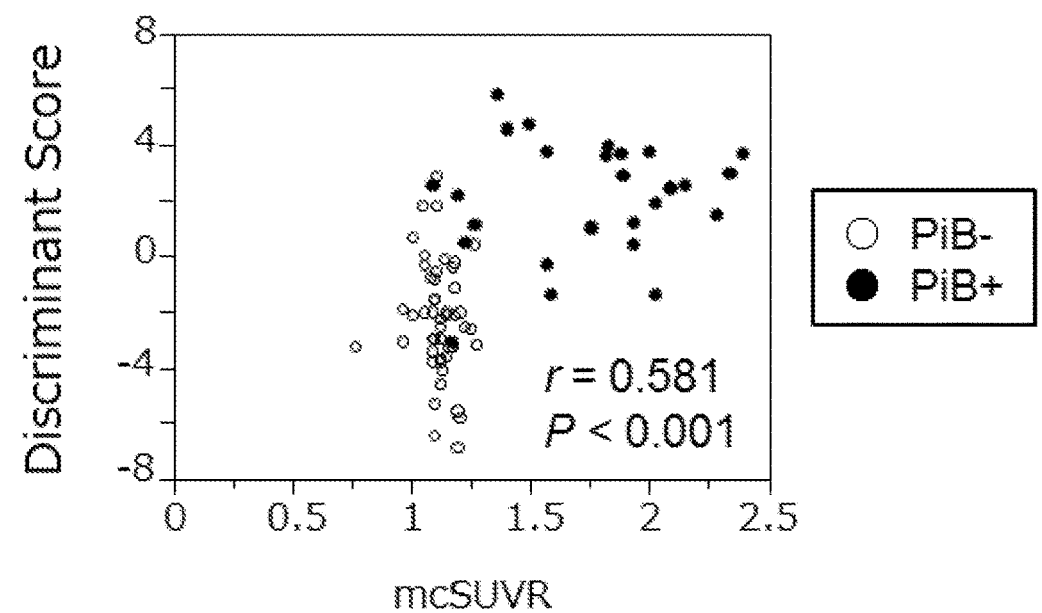
FIG. 20 is a scatter diagram of PiB accumulation mean value (mcSUVR) and discriminant score of a combination of two markers: Aβ1-40/Aβ1-42 and APP669-711/Aβ1-42 in Experimental Example 1.
Figure 21:
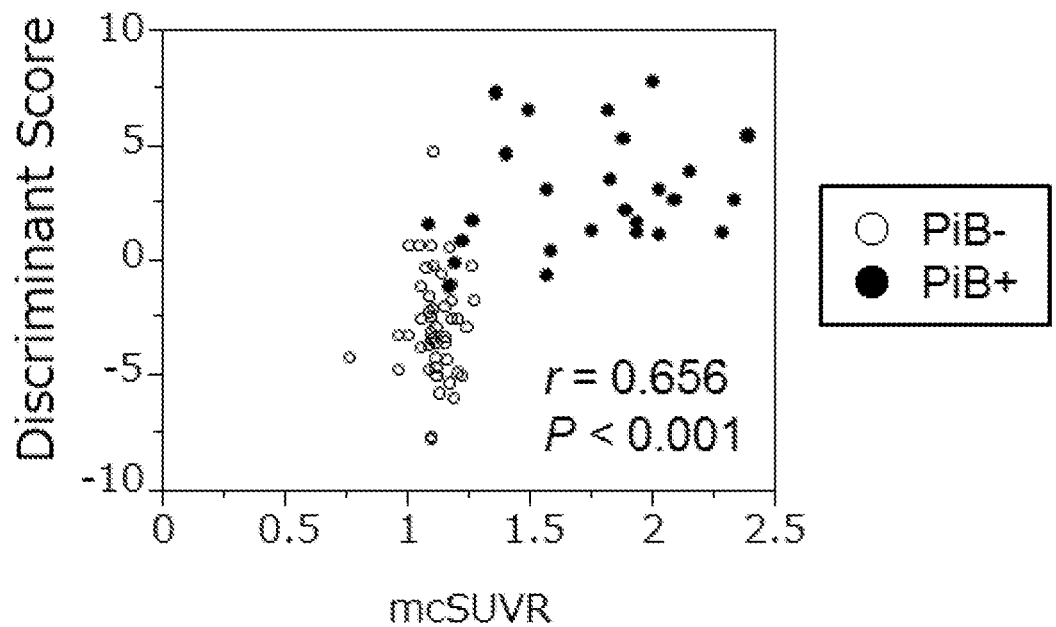
FIG. 21 is a scatter diagram of PiB accumulation mean value (mcSUVR) and discriminant score of a combination of Aβ1-39/Aβ1-42, Aβ1-40/Aβ1-42, and APP669-711/Aβ1-42 in Experimental Example 1.

FIG. 18 is a scatter diagram for a combination of two markers: Aβ1-39/Aβ1-42 and Aβ1-40/Aβ1-42, in which the horizontal axis represents PiB accumulation mean value (mcSUVR) and the vertical axis represents discriminant score of a combination of Aβ1-39/Aβ1-42 and Aβ1-40/Aβ1-42. Likewise, FIG. 19 is a scatter diagram for a combination of two markers: Aβ1-39/Aβ1-42 and APP669-711/Aβ1-42, in which the horizontal axis represents PiB accumulation mean value (mcSUVR) and the vertical axis represents discriminant score of a combination of Aβ1-39/Aβ1-42 and APP669-711/Aβ1-42. FIG. 20 is a scatter diagram for a combination of two markers: Aβ1-40/Aβ1-42 and APP669-711/Aβ1-42, in which the horizontal axis represents PiB accumulation mean value (mcSUVR) and the vertical axis represents discriminant score of a combination of two markers: Aβ1-40/Aβ1-42 and APP669-711/Aβ1-42. FIG. 21 is a scatter diagram for a combination of three markers: Aβ1-39/Aβ1-42, Aβ1-40/Aβ1-42 and APP669-711/Aβ1-42, in which the horizontal axis represents PiB accumulation mean value (mcSUVR) and the vertical axis represents discriminant score of a combination of Aβ1-39/Aβ1-42, Aβ1-40/Aβ1-42 and APP669-711/Aβ1-42.

Experimental Example 2

[2-1. Method for Combining Markers Using Normalization Based on Distribution of all Specimens]

In combining respective values of markers, the combined value is greatly influenced by a marker having a larger value if the values are directly averaged or summed. For combining the markers equally, first, normalization was conducted for each of Aβ1-39/Aβ1-42, Aβ1-40/Aβ1-42, and APP669-711/Aβ1-42 based on distribution of all the 76 cases. Normalization was conducted by calculating mean value (X) and standard deviation (S) of marker values of all the 76 cases, and converting marker value ($x_i$) of each sample into z-score ($z_i$) according to the following formula.

$$z_i=(x_i-X)/s$$

After averaging z-scores of markers to be combined, the following statistical analysis was conducted.

Combinations of two markers, Aβ1-39/Aβ1-42 and Aβ1-40/Aβ1-42, Aβ1-39/Aβ1-42 and APP669-711/Aβ1-42, and Aβ1-40/Aβ1-42 and APP669-711/Aβ1-42, as well as a combination of three markers, Aβ1-39/Aβ1-42, Aβ1-40/Aβ1-42 and APP669-711/Aβ1-42 were implemented.

[2-2. Comparison Between Groups by Combination of Markers]

For z-score of each combination of markers, comparison between the groups PiB− and PiB+ was conducted (FIGS. 22, 23, 24, 25). Any P value obtained in the t-test satisfied P<0.001, and it was confirmed that even in the case of combination, the value increased statistically significantly in the group PiB+ compared with the group PiB−.

Figure 22:
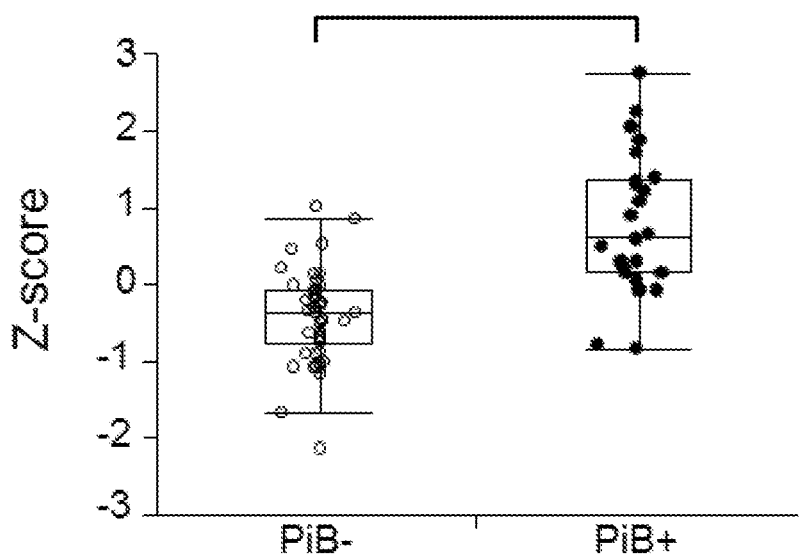
FIG. 22 is a box-and-whisker plot showing comparison between the group PiB− and the group PiB+ for a combination of two markers: Aβ1-39/Aβ1-42 and Aβ1-40/Aβ1-42 in Experimental Example 2.
Figure 23:
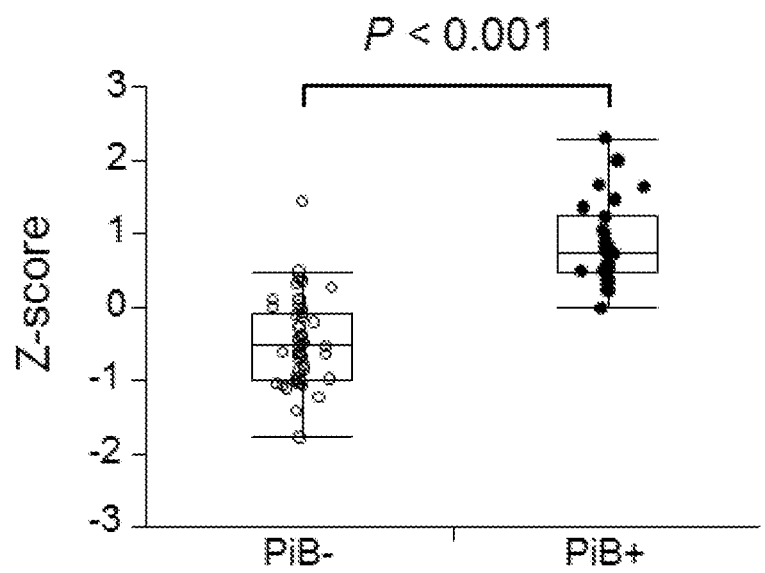
FIG. 23 is a box-and-whisker plot showing comparison between the group PiB− and the group PiB+ for a combination of two markers: Aβ1-39/Aβ1-42 and APP669-711/Aβ1-42 in Experimental Example 2.
Figure 24:
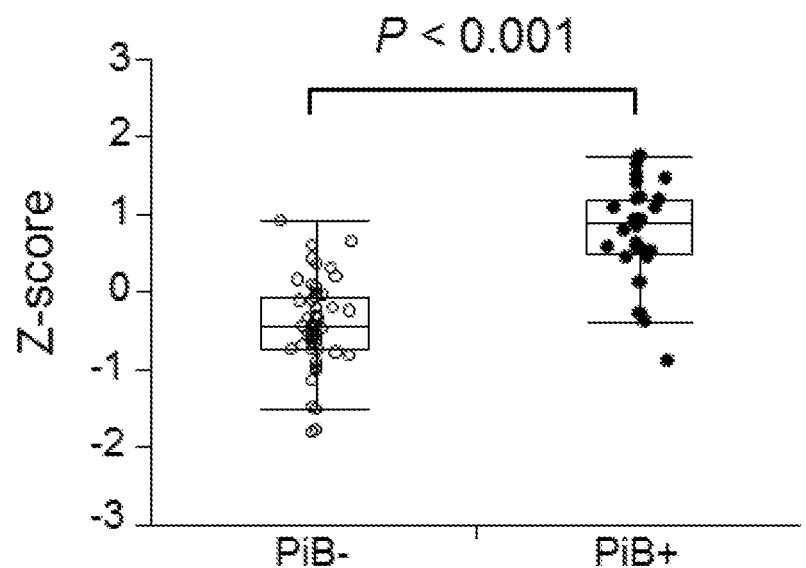
FIG. 24 is a box-and-whisker plot showing comparison between the group PiB− and the group PiB+ for a combination of two markers: Aβ1-40/Aβ1-42 and APP669-711/Aβ1-42 in Experimental Example 2.
Figure 25:
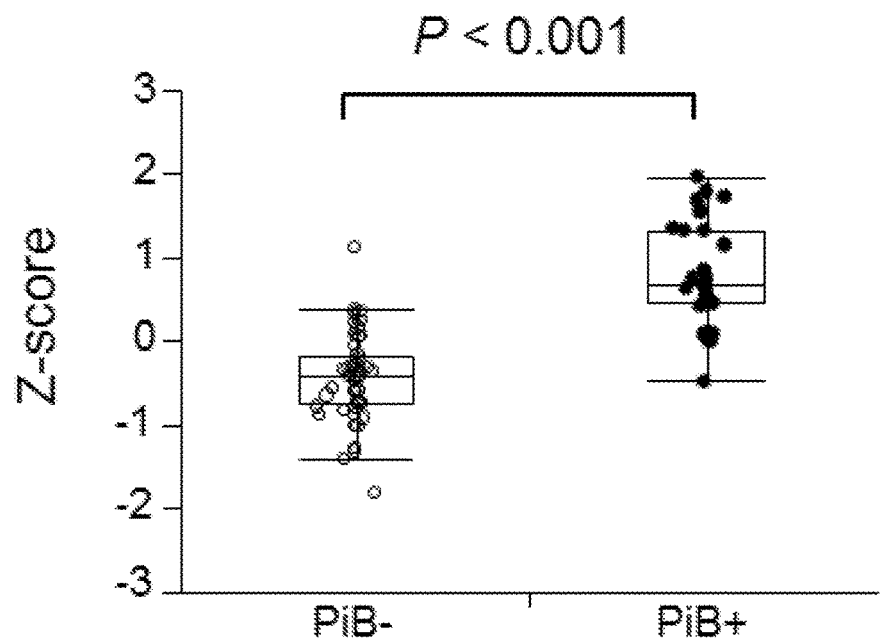
FIG. 25 is a box-and-whisker plot showing comparison between the group PiB− and the group PiB+ for a combination of three markers: Aβ1-39/Aβ1-42, Aβ1-40/Aβ1-42, and APP669-711/Aβ1-42 in Experimental Example 2.

FIG. 22 is a box-and-whisker plot showing comparison between the group PiB− and the group PiB+ for a combination of two markers: Aβ1-39/Aβ1-42 and Aβ1-40/Aβ1-42. Likewise, FIG. 23 is a box-and-whisker plot showing comparison between the group PiB− and the group PiB+ for a combination of two markers: Aβ1-39/Aβ1-42 and APP669-711/Aβ1-42. FIG. 24 is a box-and-whisker plot showing comparison between the group PiB− and the group PiB+ for a combination of two markers: Aβ1-40/Aβ1-42 and APP669-711/Aβ1-42. FIG. 25 is a box-and-whisker plot showing comparison between the group PiB− and the group PiB+ for a combination of three markers: Aβ1-39/Aβ1-42, Aβ1-40/Aβ1-42 and APP669-711/Aβ1-42.

[2-3. ROC Analysis by Combination of Markers]

Figure 26:
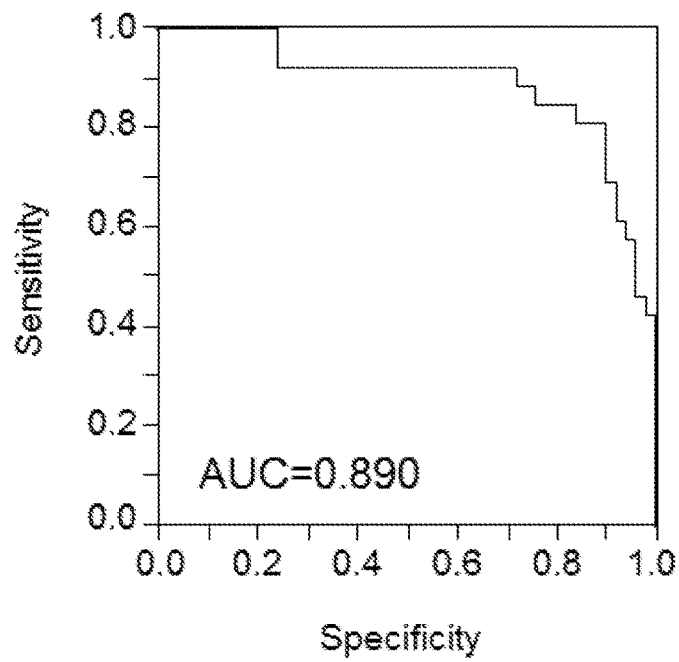
FIG. 26 is an ROC curve for a combination of two markers: Aβ1-39/Aβ1-42 and Aβ1-40/Aβ1-42 in Experimental Example 2.
Figure 27:
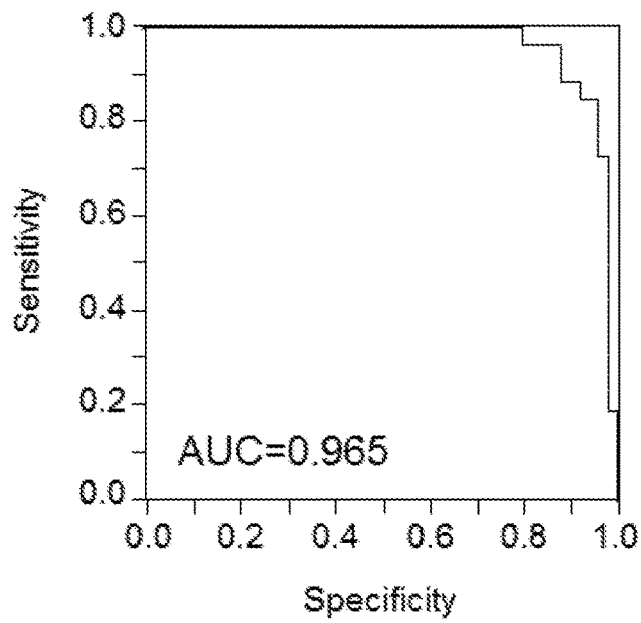
FIG. 27 is an ROC curve for a combination of two markers: Aβ1-39/Aβ1-42 and APP669-711/Aβ1-42 in Experimental Example 2.
Figure 28:
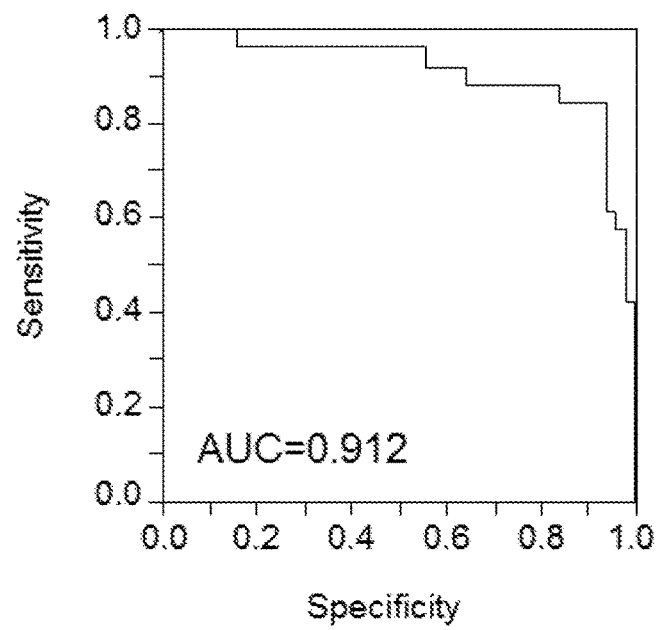
FIG. 28 is an ROC curve for a combination of two markers: Aβ1-40/Aβ1-42 and APP669-711/Aβ1-42 in Experimental Example 2.
Figure 29:
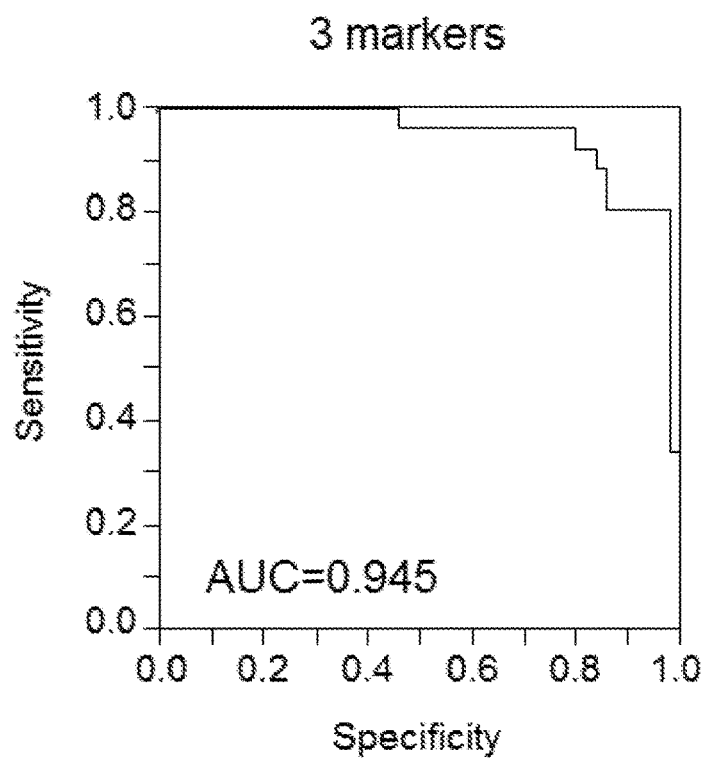
FIG. 29 is an ROC curve for a combination of three markers: Aβ1-39/Aβ1-42, Aβ1-40/Aβ1-42, and APP669-711/Aβ1-42 in Experimental Example 2.

For evaluating the determination performance of combined markers, ROC analysis of the group PiB+ versus the group PiB− was conducted with PiB+ as positive (FIGS. 26, 27, 28, 29). As a result, combinations of two makers, Aβ1-39/Aβ1-42 and APP669-711/Aβ1-42 (FIG. 27), Aβ1-40/Aβ1-42 and APP669-711/Aβ1-42 (FIG. 28), and a combination of three markers (FIG. 29) showed an AUC of 0.9 or more, which is higher than that by a single marker (FIGS. 27, 28, 29, Table 3). That is, by combining markers, the discrimination performance improved and discrimination between PiB− and PiB+ with very high accuracy was enabled. In the present ROC analysis, the combination of Aβ1-39/Aβ1-42 and APP669-711/Aβ1-42 showed the highest AUC.

FIG. 26 is an ROC curve for a combination of two markers: Aβ1-39/Aβ1-42 and Aβ1-40/Aβ1-42. Likewise, FIG. 27 is an ROC curve for a combination of two markers: Aβ1-39/Aβ1-42 and APP669-711/Aβ1-42. FIG. 28 is an ROC curve for a combination of two markers: Aβ1-40/Aβ1-42 and APP669-711/Aβ1-42. FIG. 29 is an ROC curve for a combination of three markers: Aβ1-39/Aβ1-42, Aβ1-40/Aβ1-42 and APP669-711/Aβ1-42.

In an ROC curve of each combination, the value showing the highest "sensitivity+specificity-1" was set as a cut-off value. The set cut-off values, and Sensitivity, Specificity, and Accuracy at each cut-off value are shown in Table 3 (Numbers: 21, 22, 23, 24). All the combinations showed Accuracy that is higher than that by a single marker. That is, by combining markers, the probability of exact determination was improved. In the present analysis, the combination of three markers showed the highest Accuracy. In Table 3, Numbers 21 to 24 show the results obtained by normalizing each marker value based on distribution of all the specimens, and then using an averaged value of markers to be combined for analysis.

TABLE 3

| No. | Combination of Markers | | | AUC | Correlation coefficient (r) | Cut-off | Sensitivity | Specificity | Accuracy |
| --- | --- | --- | --- | --- | --- | --- | --- | --- | --- |
| | Aβ1-39/ Aβ1-42 | Aβ1-40/ Aβ1-42 | APP669-711/ Aβ1-42 | | | | | | |
| 21 | X | X | | 0.890 | 0.607 | 0.168 | 0.808 | 0.900 | 0.868 |
| 22 | X | | X | 0.965 | 0.649 | 0.223 | 0.962 | 0.880 | 0.908 |
| 23 | | X | X | 0.912 | 0.585 | 0.453 | 0.846 | 0.940 | 0.908 |
| 24 | X | X | X | 0.945 | 0.650 | 0.434 | 0.808 | 0.980 | 0.921 |

[2-4. Correlation Analysis with mcSUVR by Combination of Markers]

In order to investigate whether z-scores of combined markers reflect a cerebral amyloid accumulation amount, correlation between each z-score and mcSUVR was analyzed. Combinations of two markers, Aβ1-39/Aβ1-42 and APP669-711/Aβ1-42, and Aβ1-40/Aβ1-42 and APP669-711/Aβ1-42, as well as a combination of three markers each showed improved Pearson product-moment correlation coefficient (r) as compared with that by a single marker, and reflected the PiB accumulation degree more favorably (FIGS. 30, 31, 32, 33, Table 3). In the present correlation analysis, the combination of three markers showed the highest correlation coefficient.

Figure 30:
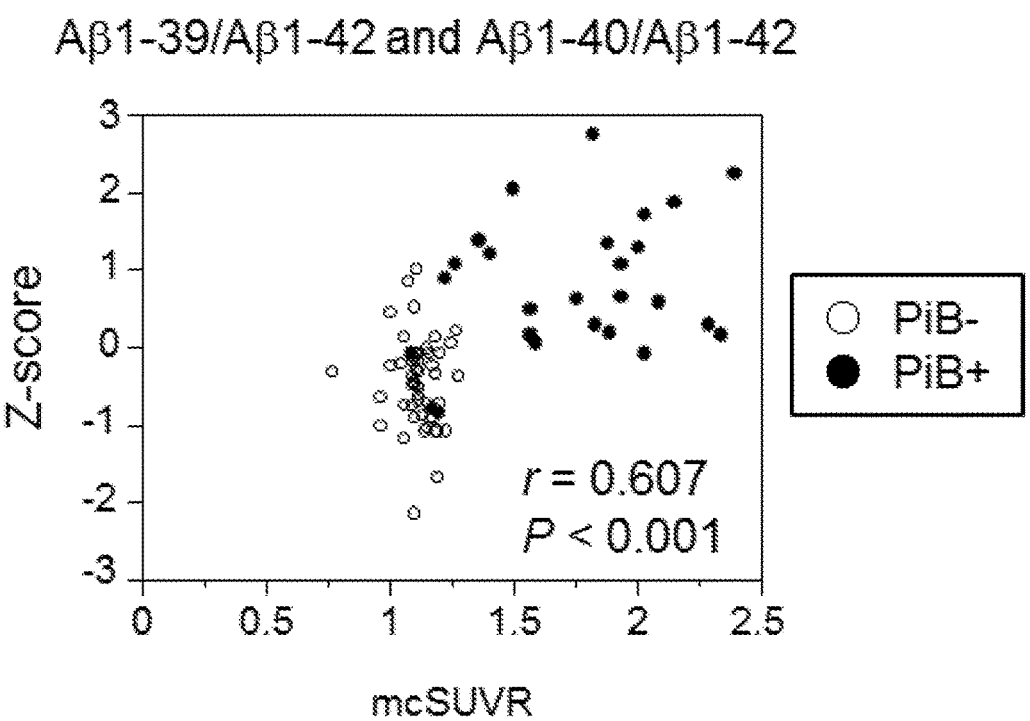
FIG. 30 is a scatter diagram of PiB accumulation mean value (mcSUVR) and z-score of a combination of Aβ1-39/Aβ1-42 and Aβ1-40/Aβ1-42 in Experimental Example 2.
Figure 31:
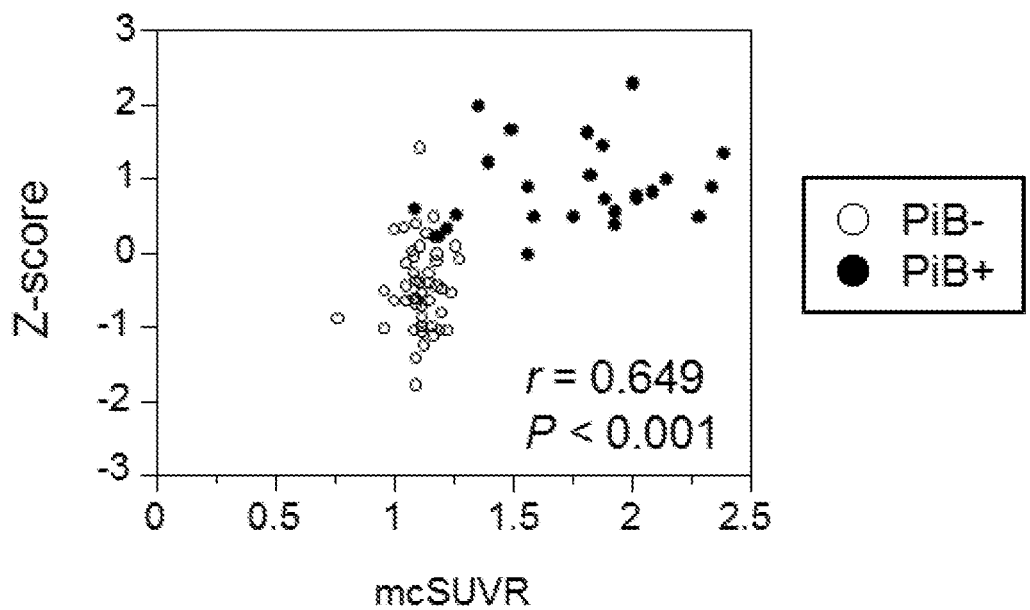
FIG. 31 is a scatter diagram of PiB accumulation mean value (mcSUVR) and z-score of a combination of Aβ1-39/Aβ1-42 and APP669-711/Aβ1-42 in Experimental Example 2.
Figure 32:
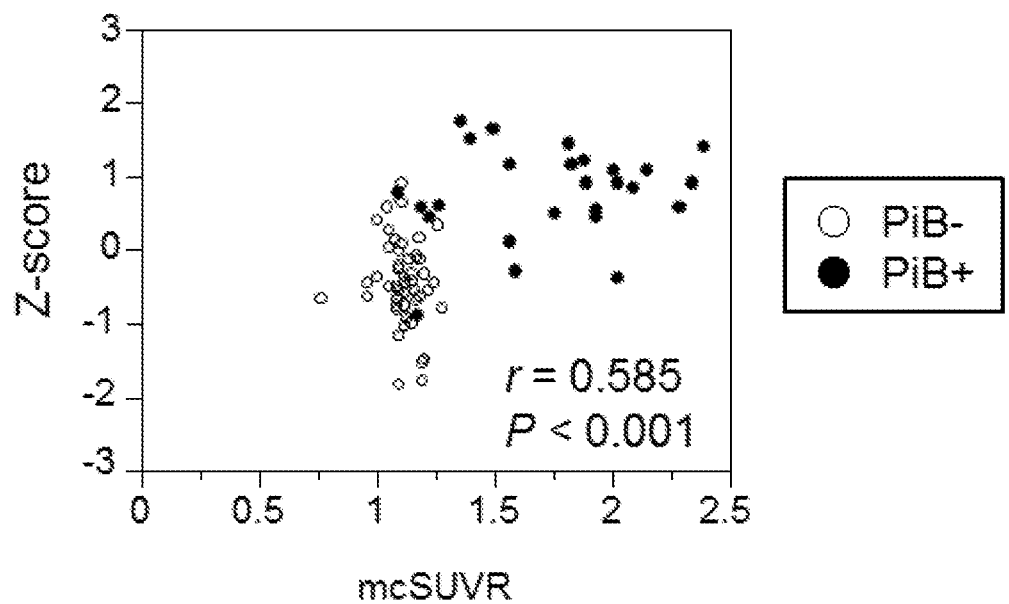
FIG. 32 is a scatter diagram of PiB accumulation mean value (mcSUVR) and z-score of a combination of Aβ1-40/Aβ1-42 and APP669-711/Aβ1-42 in Experimental Example 2.
Figure 33:
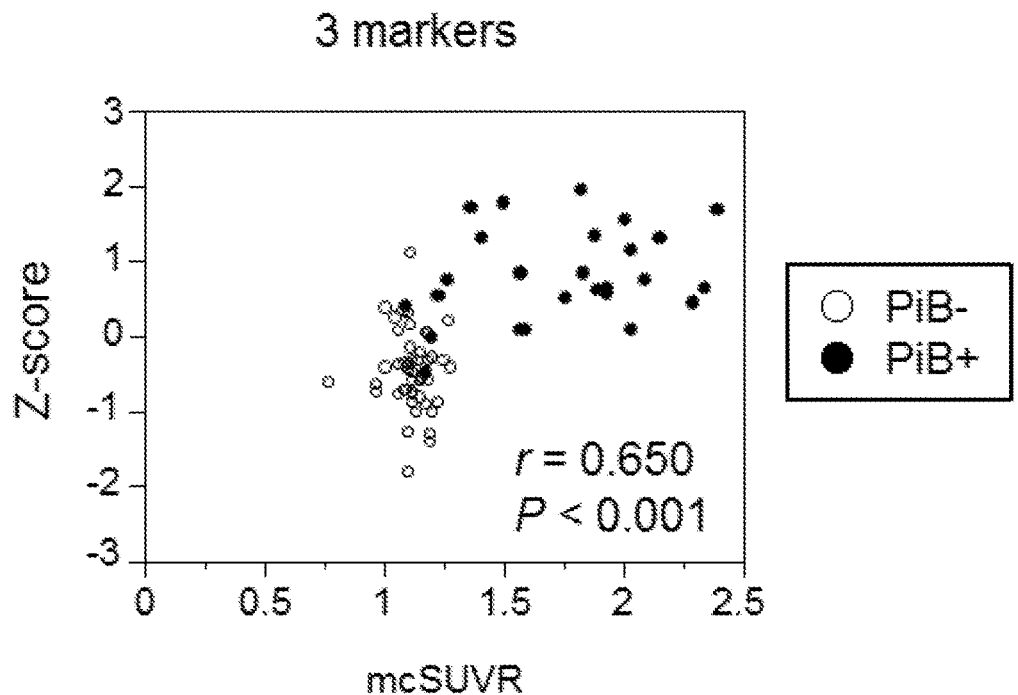
FIG. 33 is a scatter diagram of PiB accumulation mean value (mcSUVR) and z-score of a combination of Aβ1-39/Aβ1-42, Aβ1-40/Aβ1-42, and APP669-711/Aβ1-42 in Experimental Example 2.

FIG. 30 is a scatter diagram for a combination of two markers: Aβ1-39/Aβ1-42 and Aβ1-40/Aβ1-42, in which the horizontal axis represents PiB accumulation mean value (mcSUVR) and the vertical axis represents z-score of a combination of Aβ1-39/Aβ1-42 and Aβ1-40/Aβ1-42. Likewise, FIG. 31 is a scatter diagram for a combination of two markers: Aβ1-39/Aβ1-42 and APP669-711/Aβ1-42, in which the horizontal axis represents PiB accumulation mean value (mcSUVR) and the vertical axis represents z-score of a combination of Aβ1-39/Aβ1-42 and APP669-711/Aβ1-42. FIG. 32 is a scatter diagram for a combination of two markers: Aβ1-40/Aβ1-42 and APP669-711/Aβ1-42, in which the horizontal axis represents PiB accumulation mean value (mcSUVR) and the vertical axis represents z-score of a combination of Aβ1-40/Aβ1-42 and APP669-711/Aβ1-42. FIG. 33 is a scatter diagram for a combination of three markers: Aβ1-39/Aβ1-42, Aβ1-40/Aβ1-42 and APP669-711/Aβ1-42, in which the horizontal axis represents PiB accumulation mean value (mcSUVR) and the vertical axis represents z-score of a combination of Aβ1-39/Aβ1-42, Aβ1-40/Aβ1-42 and APP669-711/Aβ1-42.

Experimental Example 3

[3-1. Method for combining markers using normalization based on distribution of control group]

In Experimental Example 2, for combining each marker value, normalization was conducted based on distribution of 76 cases including all of the group PiB− and the group PiB+. In this Experimental Example 3, normalization based on distribution of 50 cases of the group PiB− as a control was conducted, and evaluation of combination was conducted. Normalization was conducted by calculating mean value (X) and standard deviation (S) of marker values of 50 cases of the group PiB−, and converting each marker value (xi) into z-score (zi) according to the following formula.

$$z_i = (x_i - X)/S$$

After averaging z-scores of markers to be combined, the following statistical analysis was conducted.

As is the case with Experimental Example 2, combinations of two markers, Aβ1-39/Aβ1-42 and Aβ1-40/Aβ1-42, Aβ1-39/Aβ1-42 and APP669-711/Aβ1-42, and Aβ1-40/Aβ1-42 and APP669-711/Aβ1-42, as well as a combination of three markers, Aβ1-39/Aβ1-42, Aβ1-40/Aβ1-42 and APP669-711/Aβ1-42 were implemented.

[3-2. Comparison Between Groups by Combination of Markers]

For z-score of each combination of markers, comparison between the groups PiB− and PiB+ was conducted (FIGS. 34, 35, 36, 37). Any P value obtained in the t-test satisfied P<0.001. Statistically significant increase in PiB+ compared with PiB− was observed even when normalization based on the group PiB− was used.

Figure 34:
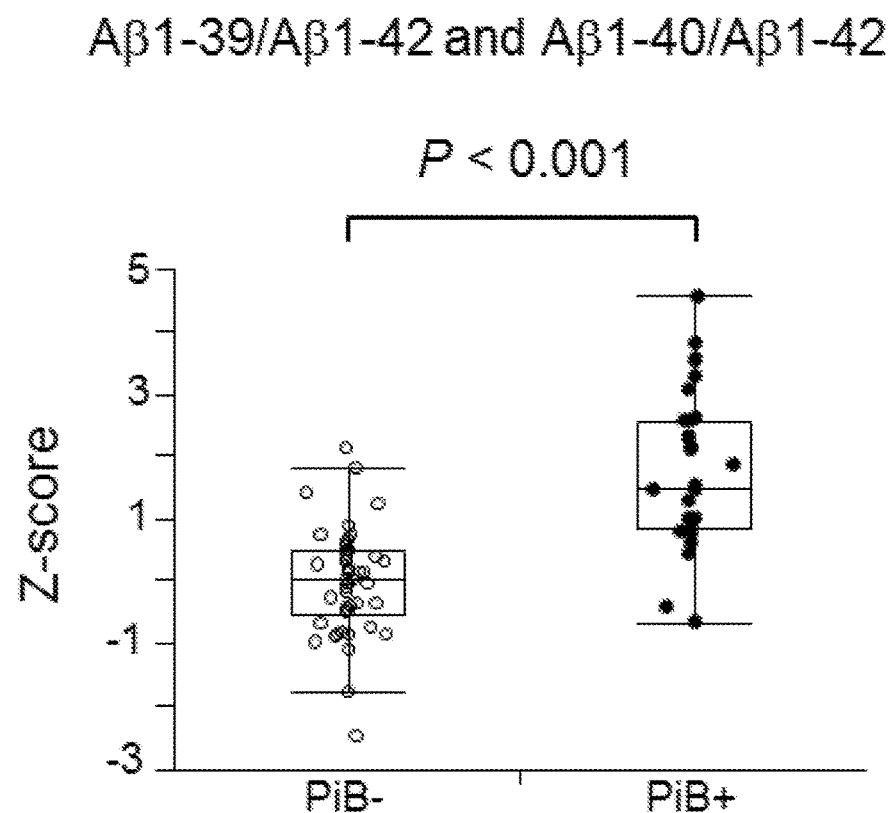
FIG. 34 is a box-and-whisker plot showing comparison between the group PiB− and the group PiB+ for a combination of two markers: Aβ1-39/Aβ1-42 and Aβ1-40/Aβ1-42 in Experimental Example 3.
Figure 35:
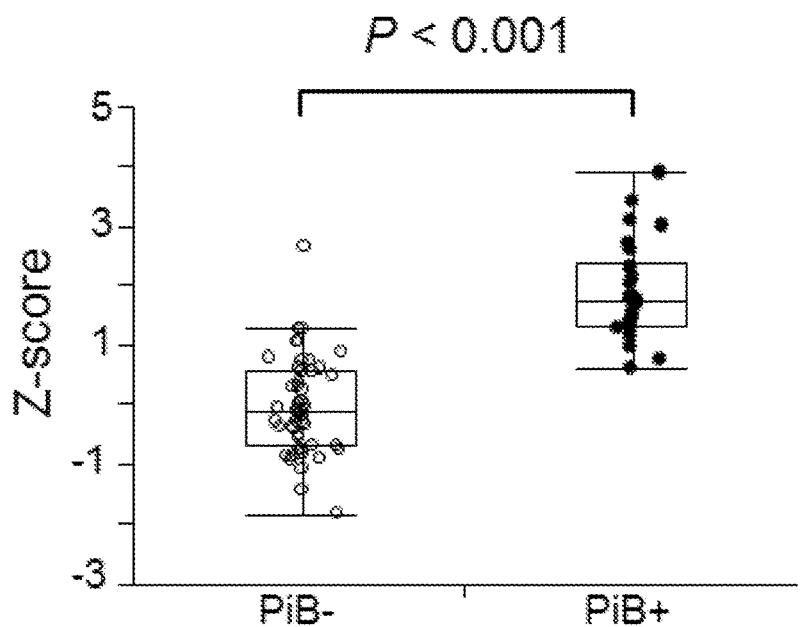
FIG. 35 is a box-and-whisker plot showing comparison between the group PiB− and the group PiB+ for a combination of two markers: Aβ1-39/Aβ1-42 and APP669-711/Aβ1-42 in Experimental Example 3.
Figure 36:
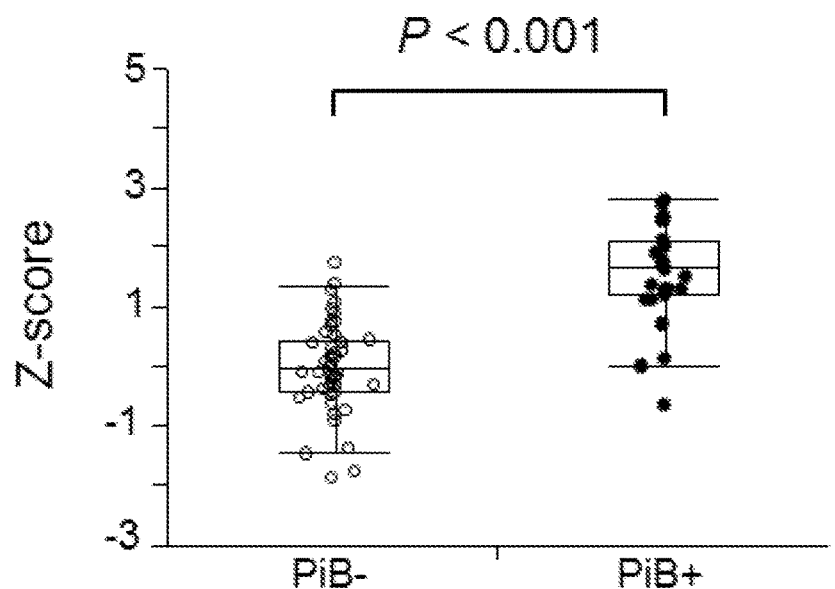
FIG. 36 is a box-and-whisker plot showing comparison between the group PiB− and the group PiB+ for a combination of two markers: Aβ1-40/Aβ1-42 and APP669-711/Aβ1-42 in Experimental Example 3.
Figure 37:
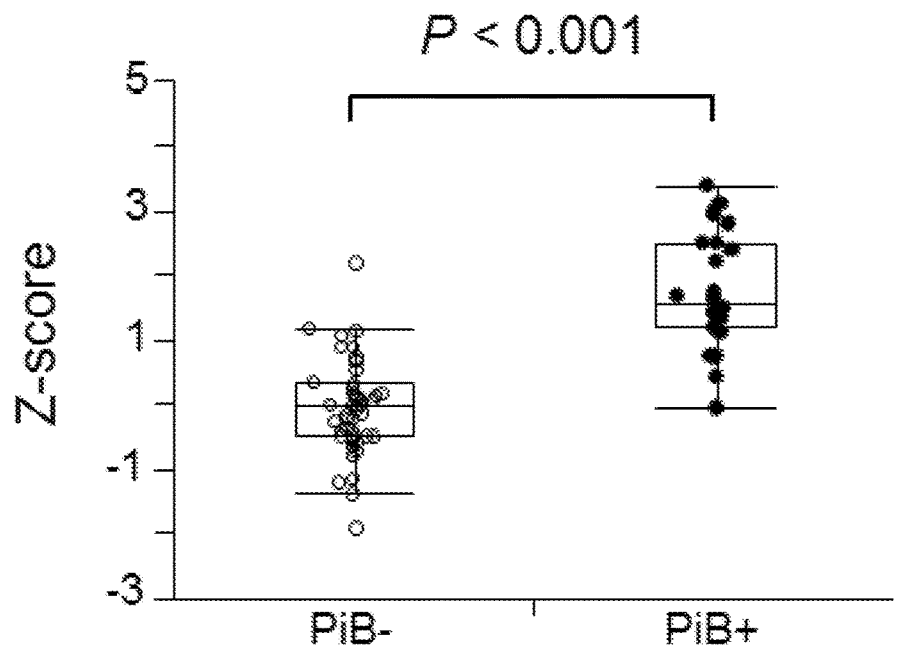
FIG. 37 is a box-and-whisker plot showing comparison between the group PiB− and the group PiB+ for a combination of three markers: Aβ1-39/Aβ1-42, Aβ1-40/Aβ1-42, and APP669-711/Aβ1-42 in Experimental Example 3.

FIG. 34 is a box-and-whisker plot showing comparison between the group PiB− and the group PiB+ for a combination of two markers: Aβ1-39/Aβ1-42 and Aβ1-40/Aβ1-42. Likewise, FIG. 35 is a box-and-whisker plot showing comparison between the group PiB− and the group PiB+ for a combination of two markers: Aβ1-39/Aβ1-42 and APP669-711/Aβ1-42. FIG. 36 is a box-and-whisker plot showing comparison between the group PiB− and the group PiB+ for a combination of two markers: Aβ1-40/Aβ1-42 and APP669-711/Aβ1-42. FIG. 37 is a box-and-whisker plot showing comparison between the group PiB− and the group PiB+ for a combination of three markers: Aβ1-39/Aβ1-42, Aβ1-40/Aβ1-42 and APP669-711/Aβ1-42.

[3-3. ROC Analysis by Combination of Markers]

Figure 38:
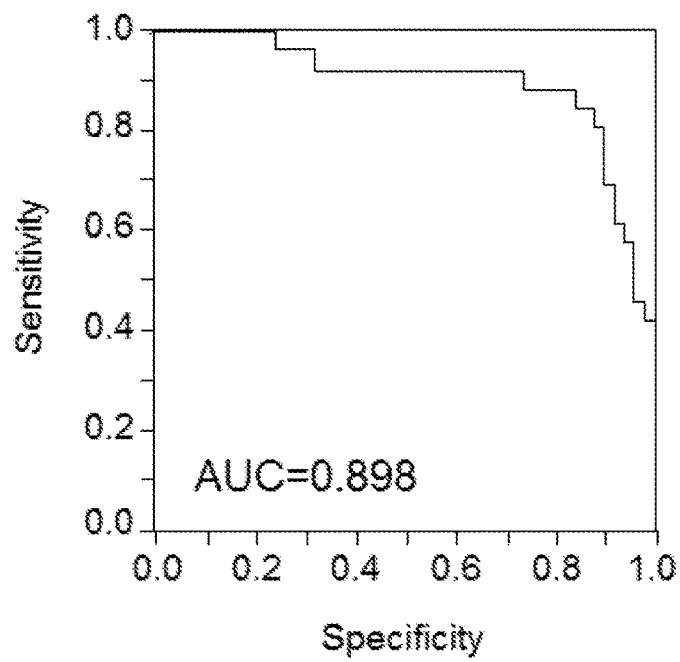
FIG. 38 is an ROC curve for a combination of two markers: Aβ1-39/Aβ1-42 and Aβ1-40/Aβ1-42 in Experimental Example 3.
Figure 39:
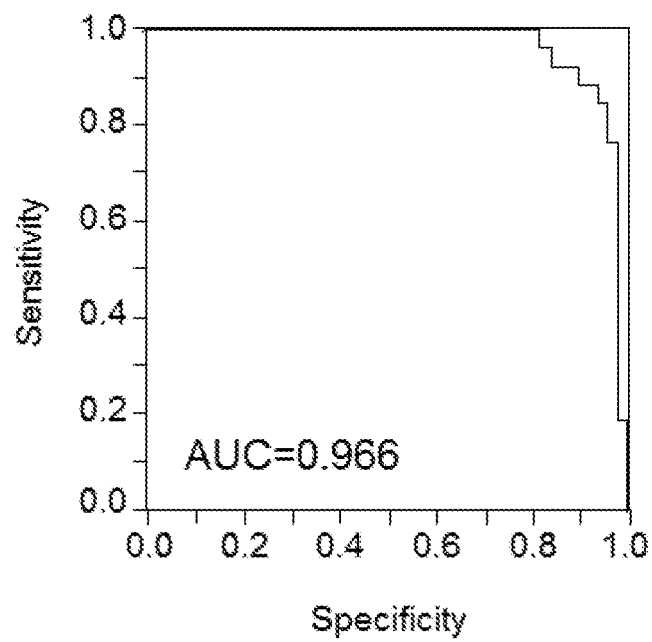
FIG. 39 is an ROC curve for a combination of two markers: Aβ1-39/Aβ1-42 and APP669-711/Aβ1-42 in Experimental Example 3.
Figure 40:
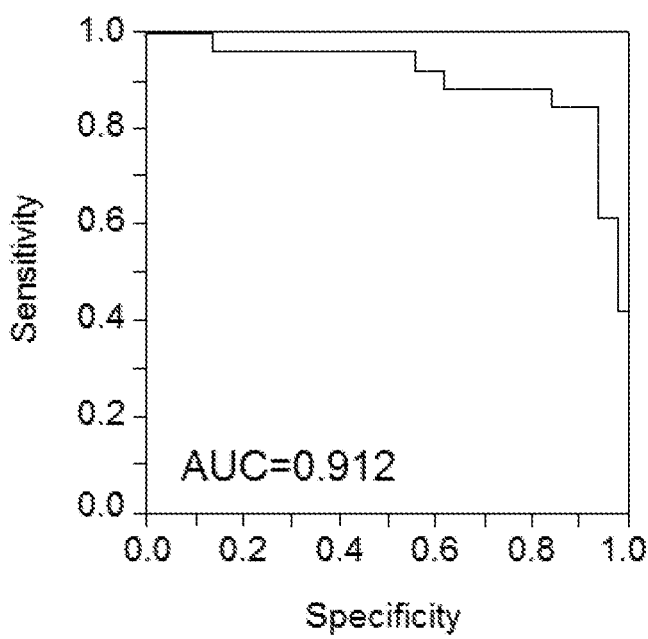
FIG. 40 is an ROC curve for a combination of two markers: Aβ1-40/Aβ1-42 and APP669-711/Aβ1-42 in Experimental Example 3.
Figure 41:
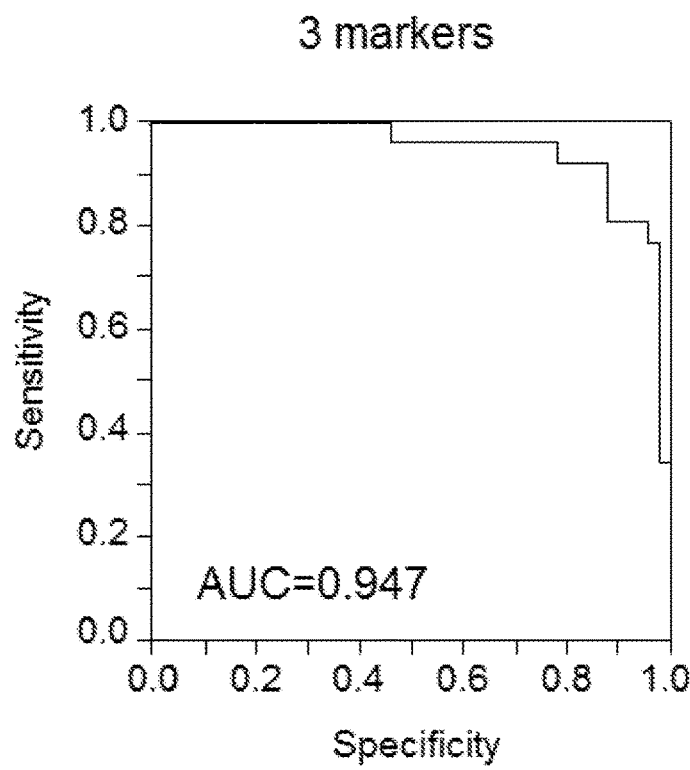
FIG. 41 is an ROC curve for a combination of three markers: Aβ1-39/Aβ1-42, Aβ1-40/Aβ1-42, and APP669-711/Aβ1-42 in Experimental Example 3.

For evaluating the determination performance of combined markers, ROC analysis of the group PiB+ versus the group PiB− was conducted with PiB+ as positive (FIGS. 38, 39, 40, 41). As a result, combinations of two makers, Aβ1-39/Aβ1-42 and APP669-711/Aβ1-42 (FIG. 39), and Aβ1-40/Aβ1-42 and APP669-711/Aβ1-42 (FIG. 40), as well as a combination of three markers (FIG. 41) showed an AUC of 0.9 or more, which is higher than that by a single marker (FIGS. 39, 40, 41, Table 4). That is, even when normalization based on the group PiB− was used, the discrimination performance improved and discrimination between PiB− and PiB+ with very high accuracy was enabled by combining markers. Also in the present ROC analysis, the combination of Aβ1-39/Aβ1-42 and APP669-711/Aβ1-42 showed the highest AUC.

FIG. 38 is an ROC curve for a combination of two markers: Aβ1-39/Aβ1-42 and Aβ1-40/Aβ1-42. Likewise, FIG. 39 is an ROC curve for a combination of two markers: Aβ1-39/Aβ1-42 and APP669-711/Aβ1-42. FIG. 40 is an ROC curve for a combination of two markers: Aβ1-40/Aβ1-42 and APP669-711/Aβ1-42. FIG. 41 is an ROC curve for a combination of three markers: Aβ1-39/Aβ1-42, Aβ1-40/Aβ1-42 and APP669-711/Aβ1-42.

In an ROC curve of each combination, the value showing the highest "sensitivity+specificity-1" was set as a cut-off value. The set cut-off values, and Sensitivity, Specificity, and Accuracy at each cut-off value are shown in Table 4. All the combinations showed Accuracy that is higher than that by a single marker. That is, by combining markers, the probability of exact determination was improved. In the present ROC analysis, the combination of Aβ1-39/Aβ1-42 and APP669-711/Aβ1-42 showed the highest Accuracy. In Table 4, Numbers 31 to 34 show the results obtained by normalizing each marker value based on distribution of 50 cases of the group PiB−, and then using an averaged value of markers to be combined for analysis.

TABLE 4

| No. | Combination of Markers | | | AUC | Correlation coefficient (r) | Cut-off | Sensitivity | Specificity | Accuracy |
| --- | --- | --- | --- | --- | --- | --- | --- | --- | --- |
| | Aβ1-39/ Aβ1-42 | Aβ1-40/ Aβ1-42 | APP669-711/ Aβ1-42 | | | | | | |
| 31 | X | X | | 0.898 | 0.612 | 0.781 | 0.846 | 0.880 | 0.868 |
| 32 | X | | X | 0.966 | 0.655 | 1.194 | 0.885 | 0.940 | 0.921 |
| 33 | | X | X | 0.912 | 0.585 | 1.154 | 0.846 | 0.940 | 0.908 |
| 34 | X | X | X | 0.947 | 0.653 | 0.748 | 0.923 | 0.880 | 0.895 |

[3-4. Correlation Analysis with mcSUVR by Combination of Markers]

In order to investigate whether z-scores of combined markers reflect a cerebral amyloid accumulation amount, correlation between each z-score and mcSUVR was analyzed. Combinations of two markers, Aβ1-39/Aβ1-42 and APP669-711/Aβ1-42, and Aβ1-40/Aβ1-42 and APP669-711/Aβ1-42, as well as a combination of three markers each showed improved Pearson product-moment correlation coefficient (r) as compared with that by a single marker (FIGS. 42, 43, 44, 45, Table 4). That is, even when normalization based on the group PiB− was used, combinations resulted in reflection of PiB accumulation degree more favorably. In the present correlation analysis, the combination of Aβ1-39/Aβ1-42 and APP669-711/Aβ1-42 showed the highest correlation coefficient.

Figure 42:
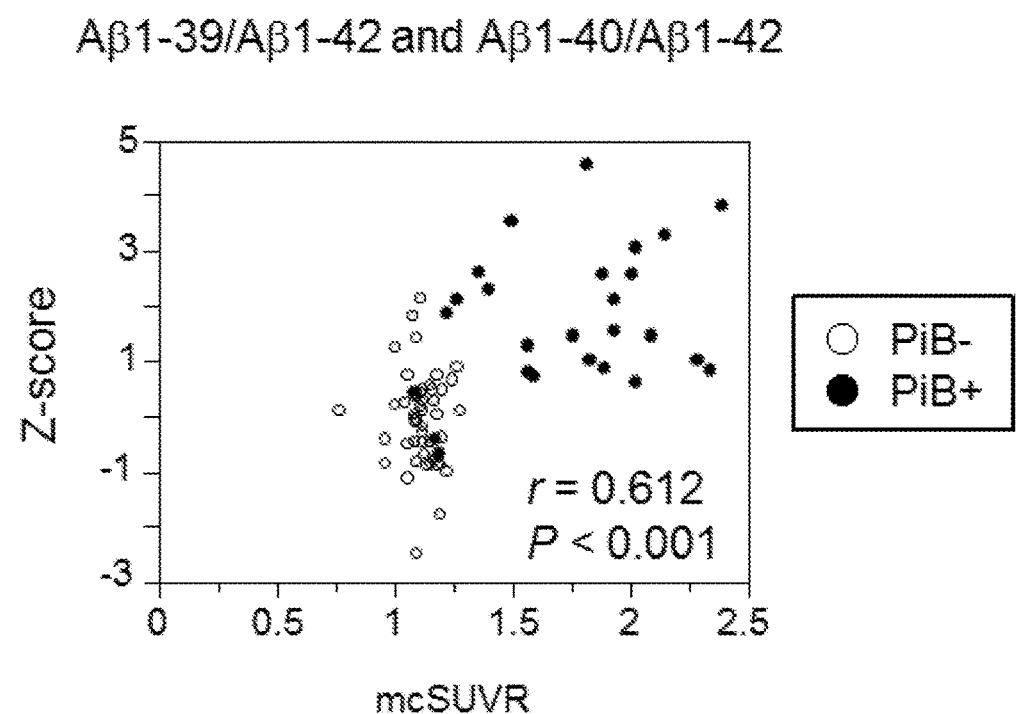
FIG. 42 is a scatter diagram of PiB accumulation mean value (mcSUVR) and z-score of a combination of Aβ1-39/Aβ1-42 and Aβ1-40/Aβ1-42 in Experimental Example 3.
Figure 43:
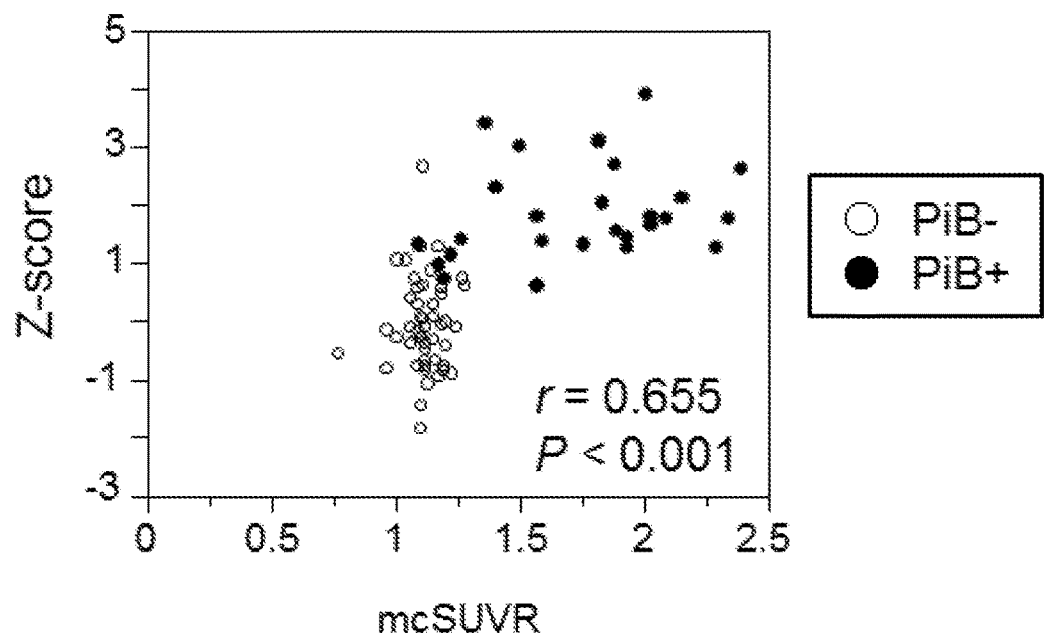
FIG. 43 is a scatter diagram of PiB accumulation mean value (mcSUVR) and z-score of a combination of Aβ1-39/Aβ1-42 and APP669-711/Aβ1-42 in Experimental Example 3.
Figure 44:
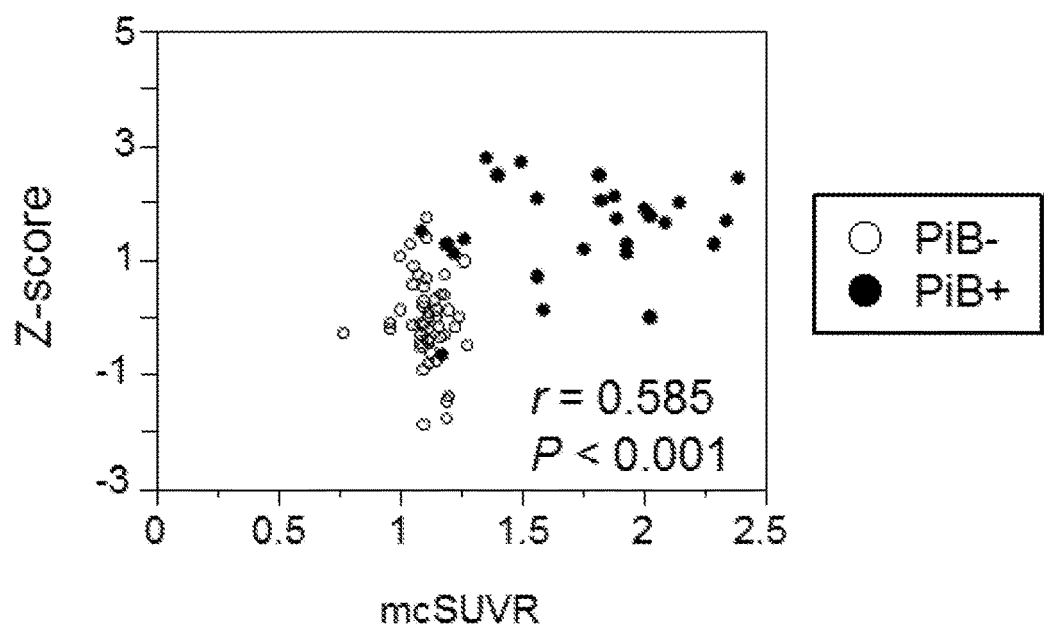
FIG. 44 is a scatter diagram of PiB accumulation mean value (mcSUVR) and z-score of a combination of two markers: Aβ1-40/Aβ1-42 and APP669-711/Aβ1-42 in Experimental Example 3.
Figure 45:
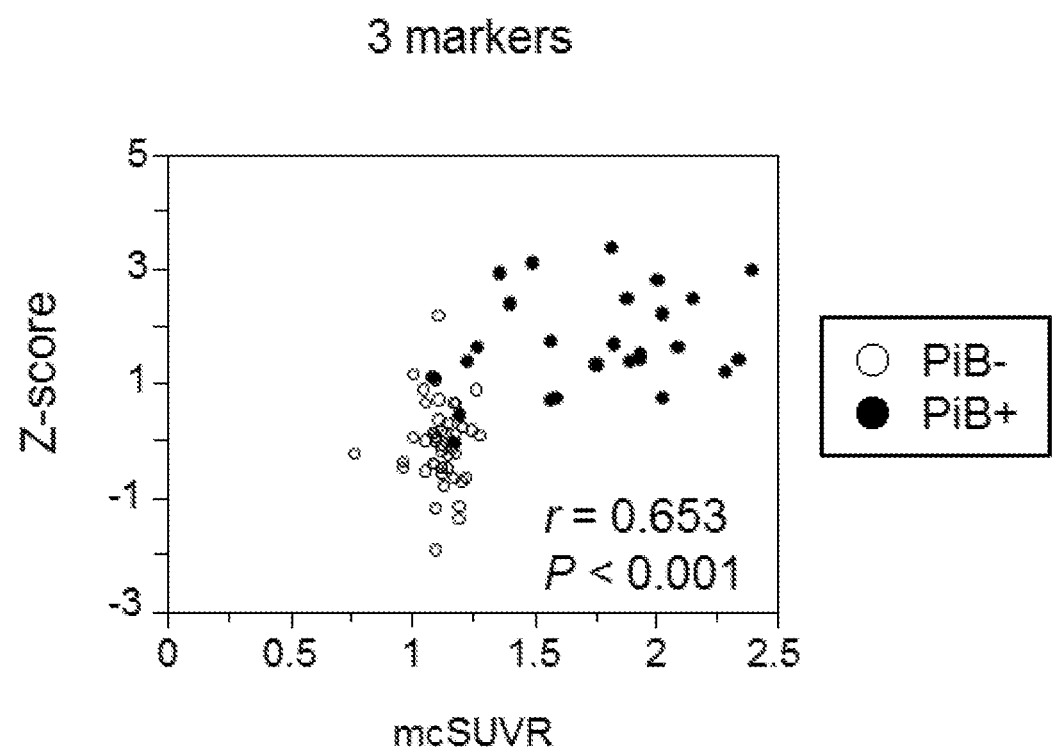
FIG. 45 is a scatter diagram of PiB accumulation mean value (mcSUVR) and z-score of a combination of Aβ1-39/Aβ1-42, Aβ1-40/Aβ1-42, and APP669-711/Aβ1-42 in Experimental Example 3.

FIG. 42 is a scatter diagram for a combination of two markers: Aβ1-39/Aβ1-42 and Aβ1-40/Aβ1-42, in which the horizontal axis represents PiB accumulation mean value (mcSUVR) and the vertical axis represents z-score of a combination of Aβ1-39/Aβ1-42 and Aβ1-40/Aβ1-42. Likewise, FIG. 43 is a scatter diagram for a combination of two markers: Aβ1-39/Aβ1-42 and APP669-711/Aβ1-42, in which the horizontal axis represents PiB accumulation mean value (mcSUVR) and the vertical axis represents z-score of a combination of Aβ1-39/Aβ1-42 and APP669-711/Aβ1-42. FIG. 44 is a scatter diagram for a combination of two markers: Aβ1-40/Aβ1-42 and APP669-711/Aβ1-42, in which the horizontal axis represents PiB accumulation mean value (mcSUVR) and the vertical axis represents z-score of a combination of two markers: Aβ1-40/Aβ1-42 and APP669-711/Aβ1-42. FIG. 45 is a scatter diagram for a combination of three markers: Aβ1-39/Aβ1-42, Aβ1-40/Aβ1-42 and APP669-711/Aβ1-42, in which the horizontal axis represents PiB accumulation mean value (mcSUVR) and the vertical axis represents z-score of a combination of Aβ1-39/Aβ1-42, Aβ1-40/Aβ1-42 and APP669-711/Aβ1-42.

These analytical results revealed that the accuracy of discrimination between PiB− and PiB+ is improved and correlation with PiB accumulation degree is enhanced by combining markers rather than using the markers singly. That is, it is shown that by combining blood markers, Aβ1-39/Aβ1-42, Aβ1-40/Aβ1-42, and APP669-711/Aβ1-42, these markers have the effects of complementarily detecting cerebral amyloid accumulation with higher accuracy. Regarding the combining method, the effect by the combination of markers was observed both by the discriminant analysis using each marker and the method of normalizing each marker value and then combining the markers. Regarding the method for normalizing each marker value, it was shown that both normalization based on all the specimens and normalization based on the group PiB− have the effect by combination of markers.

The results demonstrated above indicate that the combined marker of the present invention is useful as a blood marker for determining a cerebral Aβ accumulation state. This also has indicated the applicability to assist diagnosis of Alzheimer's disease and to presymptomatically diagnose Alzheimer's disease.

The invention claimed is:

1. A method for treating an Alzheimer patient, comprising
(a) determining a cerebral Aβ accumulation state in a subject to determine presence or stage of Alzheimer disease in the subject, comprising:
detecting, in a living body-derived sample from the subject:
Aβ1-42 (SEQ ID NO.: 3);
Aβ1-39 (SEQ ID NO.: 1); and
at least one selected from the group consisting of Aβ1-40 (SEQ ID NO.: 2), and APP669-711 (SEQ ID NO.: 4), and
obtaining (i) a ratio of Aβ1-39 level to Aβ1-42 level (Aβ1-39/Aβ1-42); and (ii) at least one ratio selected from the group consisting of: a ratio of Aβ1-40 level to Aβ1-42 level (Aβ1-40/Aβ1-42); and a ratio of APP669-711 level to Aβ1-42 level (APP669-711/Aβ1-42); and
(b) treating the subject by administering a therapeutic drug for Alzheimer, wherein the subject has a higher Aβ1-39/Aβ1-42; and (ii) a higher Aβ1-40/Aβ1-42 or APP669-711/Aβ1-42 compared to a control subject.

2. The method according to claim 1, wherein the living body-derived sample is selected from the group consisting of blood, cerebrospinal fluid, urine, and feces.

3. The method according to claim 1, wherein the living body-derived sample is blood.

4. The method according to claim 1, wherein the determining a cerebral Aβ accumulation state comprises detecting said Aβ1-40 (SEQ ID NO.: 2).

5. The method according to claim 1, wherein the determining a cerebral Aβ accumulation state comprises detecting said APP669-711 (SEQ ID NO.: 4).

6. The method according to claim 1, wherein the determining a cerebral Aβ accumulation state comprises detecting said Aβ1-40 (SEQ ID NO.: 2) and said APP669-711 (SEQ ID NO.: 4).

7. The method according to claim 1, wherein the determining a cerebral Aβ accumulation state comprises obtaining said Aβ1-40/Aβ1-42.

8. The method according to claim 1, wherein the determining a cerebral Aβ accumulation state comprises obtaining said APP669-711/Aβ1-42.

9. The method according to claim 1, wherein the determining a cerebral Aβ accumulation state comprises obtaining said Aβ1-40/Aβ1-42 and said APP669-711/Aβ1-42.

10. The method according to claim 1, wherein step (a) determines the presence of the Alzheimer disease.

11. The method according to claim 1, wherein step (a) determines the stage of the Alzheimer disease.

12. The method according to claim 1, wherein the living body-derived sample is plasma.

13. The method according to claim 1, wherein the detecting is performed by a mass spectrometer.

14. The method according to claim 1, wherein the living body-derived sample is blood;
the determining a cerebral Aβ accumulation state comprises detecting said APP669-711 (SEQ ID NO.: 4) and obtaining said APP669-711/Aβ1-42; the detecting is performed by a mass spectrometer; and the subject has the higher APP669-711/Aβ1-42 compared to a control subject.

* * * * *

SEQUENCE LISTING

```
<160> NUMBER OF SEQ ID NOS: 4

<210> SEQ ID NO 1
<211> LENGTH: 39
<212> TYPE: PRT
<213> ORGANISM: Homo Sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val
        35

<210> SEQ ID NO 2
<211> LENGTH: 40
<212> TYPE: PRT
<213> ORGANISM: Homo Sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 42
<212> TYPE: PRT
<213> ORGANISM: Homo Sapiens

<400> SEQUENCE: 3

Asp Ala Glu Phe Arg His Asp Ser Gly Tyr Glu Val His His Gln Lys
1               5                   10                  15
```

```
Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 43
<212> TYPE: PRT
<213> ORGANISM: Homo Sapiens

<400> SEQUENCE: 4

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val
            35                  40
```